(12) United States Patent
Parinov et al.

(10) Patent No.: US 8,513,484 B2
(45) Date of Patent: Aug. 20, 2013

(54) FISH CANCER MODEL

(75) Inventors: Sergey Parinov, Singapore (SG); Alexander Emelyanov, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 13/533,117

(22) Filed: Jun. 26, 2012

(65) Prior Publication Data

US 2012/0270259 A1 Oct. 25, 2012

Related U.S. Application Data

(62) Division of application No. 11/995,794, filed as application No. PCT/SG2006/000202 on Jul. 18, 2006, now Pat. No. 8,242,326.

(60) Provisional application No. 60/700,310, filed on Jul. 19, 2005.

(51) Int. Cl.
*A01K 67/027* (2006.01)
*G01N 33/00* (2006.01)

(52) U.S. Cl.
USPC .................................................. 800/3; 800/20

(58) Field of Classification Search
USPC ........................................................ 800/20, 3
See application file for complete search history.

(56) References Cited

U.S. PATENT DOCUMENTS

| | | | |
|---|---|---|---|
| 7,314,968 B2 * | 1/2008 | Moon et al. | 800/20 |
| 7,525,011 B2 * | 4/2009 | Look et al. | 800/20 |
| 2005/0138677 A1 | 6/2005 | Pfister | |

FOREIGN PATENT DOCUMENTS

WO 2004023867 A2 3/2004

OTHER PUBLICATIONS

Watzinger, F. et al., "High Sequence Similarity Within ras Exons 1 and 2 in Different Mammalian Species and Phylogenetic Divergence of the ras Gene Family," Mammalian Genome, 1998, vol. 9, pp. 214-219.

Translation of Japanese Office Action dated Dec. 27, 2011 in Japanese Patent Applicatoin No. 2008-522744, 4 pages.

Thomas, R. et al., "Models for pancreatic cancer: Giant steps forward, miles to go," Drug Discovery Today: Disease Models, Elsevier, vol. 2, No. 1, pp. 27-33, Apr. 1, 2005, XP004983071.

Bos, J.L., "ras Oncogenes in Human Cancer: A Review," Cancer Research, American Association for Cancer Research, vol. 49, No. 17, Sep. 1, 1989, pp. 4682-4689, XP008071711.

Communication from European Patent Office regarding extended European Search Report dated May 3, 2010, Application No./Patent No. EP 06 76 9685.6-2405 / 1906727-PCT/SG2006000202, Temasek Life Sciences Laboratory Limited, Ref. HB/P40637EP, Supplementary European Search Report, 3 pages.

Langenau, D.M., et al. (2005), "Cre/lox-regulated transgenic zebrafish model with conditional myc-induced T cell acute lymphoblastic leukemia," PNAS 102(17):6068-6073.

Yang, H.W., et al. (2004), "Targeted expression of human MYCN selectively causes pancreatic neuroendocrine tumours in transgenic zebrafish," Cancer Research 64:7256-7262.

Park, S., et al. (2006), "Expression of oncogenic Kras in developing zebrafish pancreas: A new vertebrate model of exocrine pancreatic cancer," Gastroenterology 130(4): A35. Meeting Info: Digestive Disease Week Meeting/107th Annual Meeting of the American-Gastroenterological-Association, Los Angeles, CA, USA. May 19-24, 2006. Amer Gastroenterol Assoc. Inst.

Bailey, G.S., et al. (1996), "Fish models for environmental carcinogenesis: the rainbow trout" Environmental Health Perspectives Supplements vol. 104 Suppl 1, pp. 5-21.

Parinov, S., et al. (2004), "Tol2 transposon-mediated enhancer trap to identify developmentally regulated zebrafish genes in vivo," Developmental Dynamics 231: 449-459.

Rotchell, J.M., et al. (2001), "Structure, expression and activation of fish ras genes," Aquatic Toxicology 55:1-21.

Derwent Abstract Accession No. 93-231492/29, Class B04, JP 5-153974 A (Taiyo Fishery Co Ltd) Jun. 22, 1993.

Johnson, L. et al., "Somatic Activation of the K-ras Oncogene Causes Early Onset Lung Cancer in Mice," Nature, vol. 410, Apr. 26, 2001, pp. 1111-1116, copyright Macmillan Magazines Ltd.

* cited by examiner

*Primary Examiner* — Valarie Bertoglio
(74) *Attorney, Agent, or Firm* — Rothwell, Figg, Ernst & Manbeck, P.C.

(57) ABSTRACT

The present invention is directed to fish whose genome has integrated therein an oncogenic nucleic acid operably linked to a promoter. Methods of making the fish and methods for their use are also provided. The fish may advantageously be utilized in methods of screening for drugs or agents that modulate oncogene-mediated neoplastic or hyperplasic transformation, or that modulate sensitivity to chemotherapy or radiation therapy. Immortal tumor cells lines, methods of making immortal tumor cells lines and methods of their use are also provided.

16 Claims, 10 Drawing Sheets

```
Human c-K-ras2D:  mteyklvvvgaggvgksaltiqliqnhfvdeydptiedsyrkqvvidgetcildildtaggee     63
zgc:85725:        mteyklvvvgaggvgksaltiqliqnhfvdeydptiedsyrkqvvidgetcildildtaggee     63

Human c-K-ras2D:  ysamrdqymrtgegflcvfainntksfedihhyreqikrvkdsedvpmvlvgnkcdlpsrtvd    126
zgc:85725:        ysamrdqymrtgegflcvfainntksfedihhyreqikrvkdsedvpmvlvgnkcdlgshnvd    126

Human c-K-ras2D:  tkqaqdlarsygipfletsaktrqgvddafytlvreirkhkekmskdgkkkkkksktkcvim-    188
zgc:85725:        skqaqdlarsygipfletsaktrqgvddafytlvreirkhkekmskegkkkkkksktkcalm    188
```

FISH CANCER MODEL

CROSS-REFERENCE OF THE RELATED APPLICATION

The present application is a division of U.S. patent application Ser. No. 11/995,794 filed 15 Jan. 2008, now U.S. Pat. No. 8,242,326, which in turn is a national stage filing under 35 U.S.C. §371 of PCT/SG2006/000202, filed on 18 Jul. 2006, which in turn claims priority to U.S. provisional patent application Ser. No. 60/700,310 filed 19 Jul. 2005, each application is incorporated herein by reference.

SEQUENCE SUBMISSION

The present application is being filed along with a Sequence Listing in electronic format. The Sequence Listing is entitled 2577218SequenceListing.txt, created on 24 Apr. 2012 and is 21 kb in size. The information in the electronic format of the Sequence Listing is incorporated herein by reference in its entirety.

BACKGROUND OF THE INVENTION

The present invention is directed to fish containing an oncogenic nucleic acid, to fish tumorgenesis models, to immortal tumor cell lines and to screening for anti-cancer agents.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Animal models of disease states play an important role in identifying the underlying biochemical mechanisms of particular diseases, as well as discovering therapeutic agents to eradicate the disease or otherwise lessen its symptoms. For example, rabbit models of familial hypercholesterolemia, rat models of non-insulin-dependent diabetes mellitus, mouse models of cancer and hamster models for spontaneous atrial thrombosis are known. Additionally, animal models for genetic diseases have arisen spontaneously in a variety of species, including mice, cats and dogs. Working with such large animals poses several drawbacks. For example, many of the animals used in such models are relatively large vertebrates which take up a large amount of research space, are costly to feed and otherwise maintain, have slow reproductive cycles, produce relatively few offspring at one time, and cannot effectively mimic all desired disease states.

Transgenic fish are currently being utilized to develop disease models. A wide variety of fish may be utilized for this purpose. Exemplary fish include teleost fish, such as zebrafish (*Danio rerio*), medaka (*Oryzias latipes*), mummichog (*Fundulus heteroclitus*), killifish (Genus *Fundulus*), catfish (Genus *Ictalurus*), such as channel catfish; carp (Genus *Cyprinus*), such as common carp; and trout or salmon (e.g., Genus *Salvelinus, Salmo,* and *Oncorhynchus*). Zebrafish have become an established model for investigating many facets of development, physiology and disease.

Zebrafish are particularly advantageous because they are small, develop ex utero, and have a short generation time. Zebrafish are economical to maintain in the laboratory environment and are highly fecund; a single female is capable of generating hundreds of offspring per week. At 5 days of age each fish is a free swimming/feeding organism complete with most of the organ systems employed by mammals, such as heart, brain, blood, and pancreas. The zebrafish embryo develops externally and is transparent, allowing direct visualization of cellular and tissue developmental processes as they proceed in vivo, thereby facilitating large-scale genetic and small molecule drug screens. In the past several years numerous publications have reported transgenic fish lines expressing green fluorescent protein (GFP) in cell-type restricted expression patterns (Gong et al., 2001; Kennedy et al., 2001; Long et al., 1997; Moss et al., 1996; Motoike et al., 2000; Park et al., 2000). To date, studies using fluorescent transgenic zebrafish have focused mainly on imaging cells and tissues as they develop. Such transgenic zebrafish lines, in addition to promoting developmental investigations of tissue morphogenesis, facilitate genetic and pharmacological screens by allowing high-resolution imaging of discrete cell populations.

Many of the underlying mechanisms that lead to cancer have yet to be fully understood. Identifying the genes mutated in these diseases will lead to new insights into cancer as a whole. Additionally, using a vertebrate model system in which genetic or chemical suppressors can be identified that inhibit or delay disease progression, or sensitivity to chemotherapy or radiation-induced programmed cell death, will be necessary to identify new drug targets for the development of targeted chemotherapies. For example, a model system is needed, which does not require an a priori knowledge of the specific target. Target elucidation may be accomplished after the modulating target drug or agent is demonstrated safe and effective, which, thus, saves both time and expense in the drug discovery process.

A further understanding of the cellular and molecular genetic features of various disease states such as cancer is needed. An appropriate animal model would be invaluable to extend the understanding of cancer, as well as to enable the development of more effective drugs for treating or preventing cancer. The present invention addresses these needs.

SUMMARY OF THE INVENTION

The present invention is directed to fish containing an oncogenic nucleic acid, to fish tumorgenesis models, to immortal tumor cell lines and to screening for anti-cancer agents.

Thus, in a first aspect, the present invention provides a construct that comprises an oncogenic nucleic acid, also referred to herein as an oncogene, operably linked to a promoter. The construct preferably further comprises a marker. The construct may also be part of a vector. Preferably the promoter is an organ- or tissue-specific promoter or a minimal promoter. As known in the art, an oncogene is a gene whose expression can lead to alteration of the control of cellular proliferation or to the prevention of programmed cell death. A wide variety of oncogenes may be utilized in the nucleic acid constructs described herein. The oncogenes may be of viral or cellular origin. Oncogenes of cellular origin include endogenous oncogenes. Such oncogenes, when expressed, lead to neoplastic or hyperplastic transformation of a cell. The oncogene may be a complete sequence of the oncogene, preferably an oncogenic form of the oncogene, or it may be a fragment of the oncogene that maintains the oncogenic potential of the oncogene.

In a second aspect, the present invention provides transgenic fish, particularly transgenic zebrafish (*Danio rerio*), containing the above construct in its genome or expressing the oncogene only in some cells of the fish (random/mosaic expression).

In a third aspect, the present invention provides an immortal tumor cell line and a method of producing the immortal tumor cell line. In one embodiment, the immortal tumor cell line is produced by expressing the oncogene in fish to produce a tumor, isolating cells from the tumor and culturing the isolated tumor cells to produce an immortal tumor cell line.

In a fourth aspect, the present invention provides a method for screening compounds to identify drugs useful for treating cancer associated with the oncogenes.

BRIEF DESCRIPTION OF THE FIGURES

FIG. 1A shows alignment of human (SEQ ID NO:1) and zebrafish (SEQ ID NO:2) K-ras protein sequences. Human c-K-ras2b: GenBank accession NP_004976; version NP_004976.2; GI:15718761. *Danio rerio* Zgc:85725: GenBank accession NP_001003744; version NP_001003744.1; GI:51230608 encoded by zgc:85725 mRNA (cDNA clone MGC:85725 IMAGE:6968999) GenBank accession BC078646; GI:50925043 (Strausberg et al., 2002). The "i" represent conserved amino acid residues and the "*" represent conservative amino acid changes.

FIG. 1B shows alignment of Ras oncogenic protein family members. The 164 N-terminal amino acids of all Ras proteins are highly conserved. Only the remaining 25 C-terminal residues are highly divergent (hypervariable domain). *Danio rerio* Zgc:85725: GenBank accession NP_001003744; version NP_001003744.1; GI:51230608 (SEQ ID NO:2). Kirsten murine sarcoma virus proto-oncogene protein RNA: GenBank accession Z23152; version Z23152.1; GI:939929 (SEQ ID NO:3). Human c-K-ras2 protein isoform b: GenBank accession NP_004976; version NP_004976.2; GI:15718761 (SEQ ID NO:1). Human c-K-ras2 protein isoform a: GenBank accession NP_203524; version NP_203524.1; GI:15718763 (SEQ ID NO:4). Human transforming protein p21/H-Ras-1: GenBank accession P01112; version P01112; GI:131869 (SEQ ID NO:5). Human transforming protein N-Ras: GenBank accession P01111; version P01111; GI:131883 (SEQ ID NO:6). *Danio rerio* p21 N-ras oncogene: GenBank accession AAB40625; version AAB40625.1; GI:1778053 (SEQ ID NO:7).

FIG. 2 shows neoplastic transformation of cells in zebrafish injected with the EGFP-Ras construct and effects of various drugs.

FIGS. 3A(3B), 3F(3E) and 3G(3H) show fish having internal body tumors.

FIG. 4 shows histochemical analysis of tumor formation in $F_0$ adult fish that were injected with P-krt8-EGFP-zK-rasB transgene. Paraffin embedded sections were stained with hematoxylin/eosin.

FIG. 6 shows origin and characteristics of an example of a tumor cell line obtained from a Pkrt8-EGFP-K-rasB(V12)-induced eye tumor.

DETAILED DESCRIPTION OF THE INVENTION

Figure 2A:
FIG. 2a shows a control fish injected with P-krt8-EGFP-TAA(stop)-K-rasB(V12) construct that has a TAA stop codon preventing expression of K-RasB(V12). In this control, the EGFP-positive cells have normal morphology characteristic for P-krt8-EGFP expression.

The present invention describes fish containing an oncogenic nucleic acid, to fish tumorgenesis models, to immortal tumor cell lines and to screening for anti-cancer agents.

In one embodiment, the present invention is directed to a construct that comprises an oncogenic nucleic acid, also referred to herein as an oncogene, operably linked to a promoter. The construct preferably further comprises a marker. The construct may also be part of a vector. Preferably the promoter is an organ-specific promoter, a tissue-specific promoter or a minimal promoter. By "minimal promoter", it is meant herein that the promoter comprises the minimal sequence that comprises a functional promoter. Techniques are well known in the art for identifying minimal promoters (Baliga, 2001). As known in the art, an oncogene is a gene whose expression can lead to alteration of the control of cellular proliferation or to the prevention of programmed cell death. A wide variety of oncogenes may be utilized in the nucleic acid constructs described herein. The oncogenes may be of viral or cellular origin. Oncogenes of cellular origin include endogenous oncogenes. Such oncogenes, when expressed, lead to neoplastic or hyperplastic transformation of a cell. The oncogene may be a complete sequence of the oncogene, preferably an oncogenic form of the oncogene, or it may be a fragment of the oncogene that maintains the oncogenic potential of the oncogene.

Exemplary oncogenes include activated RAS, MYC, SRC, FOS, JUN, MYB, RAS, ABL, BCL2, HOX11, HOX11L2, TAL1/SCL, LMO1, LMO2, EGFR, MYCN, MDM2, CDK4, GLI1, IGF2, activated EGFR, mutated genes, such as FLT3-ITD, mutated and activated versions of TP53, PAX3, PAX7, BCR/ABL, HER2/NEU, FLT3R, FLT3-ITD, SRC, RAS, ABL, TAN1, PTC, B-RAF, PML-RAR.alpha., E2A-PBX1, and NPM-ALK, as well as fusion of members of the PAX and FKHR gene families.

Other exemplary oncogenes are well known in the art and several such examples are described in, for example, *The Genetic Basis of Human Cancer* (Vogelstein, B. and Kinzler, K. W. eds. McGraw-Hill, New York, N.Y., 1998). Homologues of such genes can also be used. Mammalian homologues of such genes are preferred because they can be distinguished from endogenous fish genes. Further preferred are human homologues of such genes. The corresponding sequences of such oncogenes, including the human homologues of the oncogenes, are known and may be found, for example, in the GenBank database.

The oncogene is selected based on the form of cancer it is desired that the transgenic fish will develop. For example, mutated or activated genes of the RAS family (K-, H- or N-RAS) may be used for induction of a wide variety of types of cancers, such as renal, pancreatic or colon cancers, and HOX11 and TAL1 may be used for T-cell cancer induction, etc. The invention is not limited to specific oncogene sequences. For example, altered forms of the oncogene nucleotide sequence or other oncogene nucleotide sequences described herein, that increase or decrease the transformation potential of the oncogene are also envisioned.

Figure 1B:
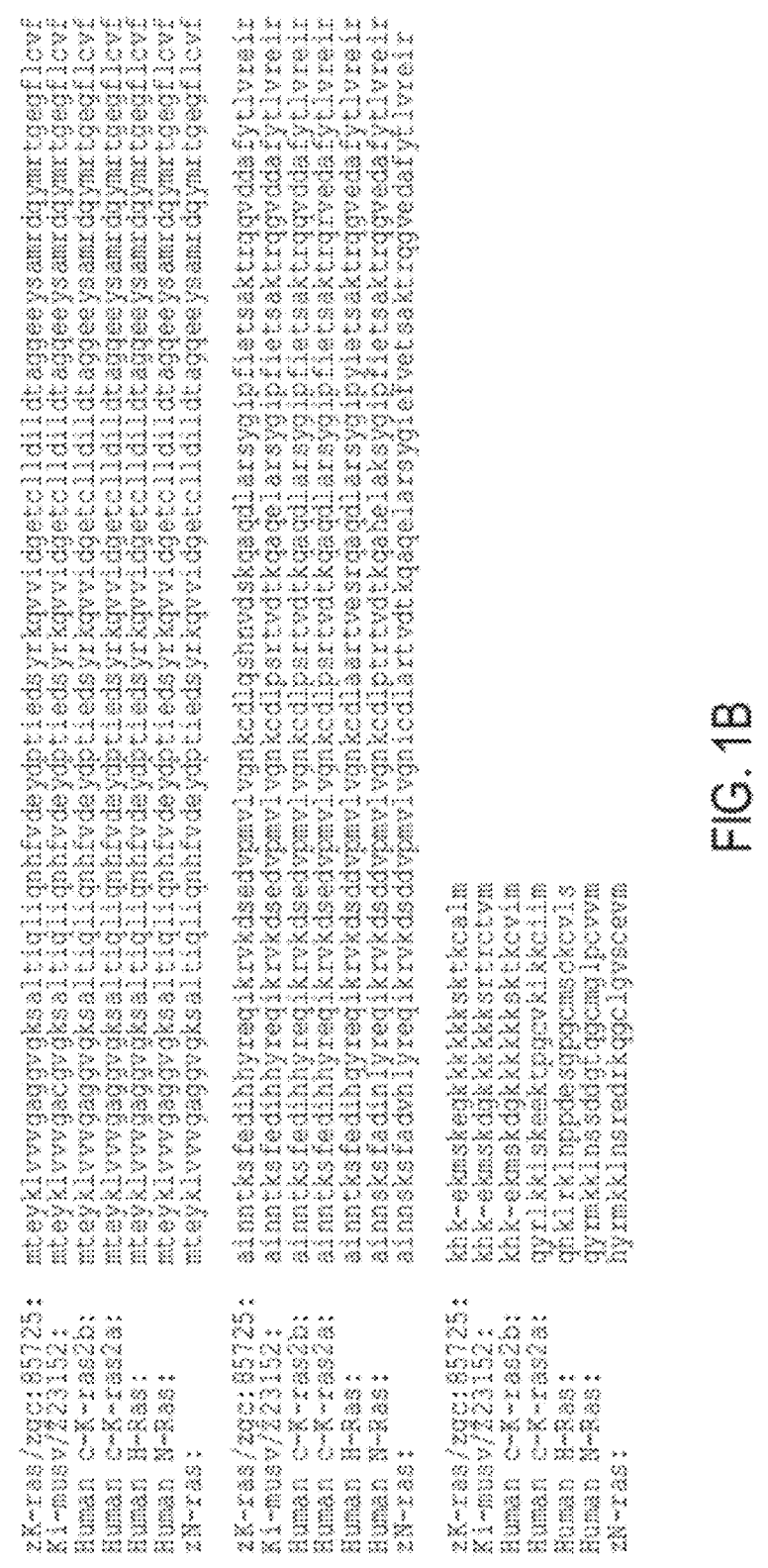

In one embodiment of the invention, the oncogene utilized in the invention encodes an oncogenic ras polypeptide sequence. The 164 N-terminal amino acids of all Ras proteins are highly conserved (FIG. 1B). Only the remaining 25 C-terminal residues are highly divergent between K-, H- and N-Ras. Oncogenic mutations that occur mainly in codons 12, 13 or 61 affect the catalytic site of GTP hydrolysis. The mutated forms of Ras remain GTP-bound and transduce constitutive signals for cell proliferation. Activating mutations in ras genes have been implicated in approximately 30% of human cancers. However, oncogenic forms of different Ras proteins are found in different types of human cancers. For example, K-Ras mutations are common in pancreatic, colon and adenocarcinomas (Bos, 1989), while hematologic malignancies harbor predominately mutations in N-Ras (Ahuja et al., 1990).

In another embodiment, the oncogene utilized in the invention encodes an oncogenic K-ras polypeptide. In an additional embodiment, the oncogene utilized in the present invention encodes a zebrafish oncogenic zK-rasB polypeptide (SEQ ID NO:8). In a further embodiment, the oncogene utilized in the invention may have at least about 60%, preferably at least about 70%, more preferably at least about 80%, and most preferably at least about 90% identity to the nucleotide sequence of the oncogenic ras nucleotide sequence or the other oncogene nucleotide sequences discussed herein when optimally aligned (with appropriate nucleotide insertions or deletions). In another embodiment, the oncogenic ras polypeptides of the present invention include the polypeptides of SEQ ID NO:8, as well as polypeptides which have at least 65% similarity (preferably at least a 65% identity), or at least 70% similarity (preferably at least a 70% identity), or at least 75% similarity (preferably at least a 75% identity), or at least 80% similarity (preferably at least a 80% identity), or at least 85% similarity (preferably at least a 85% identity), or at least 90% similarity (preferably at least a 90% identity), or at least a 95% similarity (preferably a 95% identity) to the polypeptide of SEQ ID NO:8. As known in the art "similarity" between two polypeptides is determined by comparing the amino acid sequence and its conserved amino acid substitutions of one polypeptide to the sequence of a second polypeptide.

Identity means the degree of sequence relatedness between two polypeptides or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D., *SIAM J Applied Math.* 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12:387 (1984)), BLASTP, BLASTN, FASTA (Altschul et al. (1990); Altschul et al. (1997)). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Similar considerations apply when determining the identity between two polypeptide sequences.

Additionally, the oncogene may include nucleotide sequences having substantial similarity to an oncogenic ras nucleotide sequence, or an oncogenic K-ras nucleotide sequence, or a zebrafish oncogenic zK-rasB that encodes the polypeptide set forth in SEQ ID NO:8, or the other oncogene nucleotide sequences discussed herein. By "substantial similarity", it is meant herein that the nucleotide sequence is sufficiently similar to a reference nucleotide sequence that it will hybridize therewith under moderately stringent conditions. This method of determining similarity is well known in the art to which the invention pertains. Briefly, moderately stringent conditions are defined in Sambrook et al. (*Molecular Cloning: A Laboratory Manual*, $2^{nd}$ Ed., Vol. 1, pp. 101-104, Cold Spring Harbor Laboratory Press (1989)) as including the use of a prewashing solution of 5×SSC (a sodium chloride/sodium citrate solution), 0.5% sodium dodecyl sulfate (SDS), 1.0 mM ethylene diaminetetracetic acid (EDTA)

(pH 8.0) and hybridization and washing conditions of 55° C., 5×SSC. A further requirement of the nucleotide sequence of the oncogene is that it encode a protein having cell neoplastic transformation ability. That is, the proteins have the ability to convert normal (i.e., non-cancerous cells) into cancerous cells (i.e., tumors).

The oncogene, also considered herein as the transgene, the gene which is introduced into the genome described herein, may be either synthesized in vitro or isolated from a biological source. Such methods of synthesis and isolation are well known to the skilled artisan. As used herein, the terms "transgene" or "transgene construct" or "transgenic construct" or "transgenic DNA sequence", are used interchangeably and refer to a nucleic acid molecule typically comprised of, but not limited to, regulatory regions (e.g. promoter and enhancer sequences) that are competent to initiate and otherwise regulate the expression of a gene product(s). Transgenic constructs may also contain any other mutually compatible DNA elements for controlling the expression and/or stability of the associated gene product(s), such as polyadenylation sequences. Transgenic constructs may also contain other DNA sequences which function to promote integration of operably linked DNA sequences into the genome of a zebrafish and any associated DNA elements contained in any nucleic acid system (e.g. plasmid expression vectors) used for the propagation, selection, manipulation and/or transfer of recombinant nucleic acid sequences.

Transgene constructs are the genetic material that is introduced into fish to produce a transgenic fish. As used herein the term "transgenic" refers to an organism and the progeny of such an organism that contains a DNA molecule that has been artificially introduced into the organism. The manner of introduction, and, often, the structure of a transgene construct, render such a transgene construct an exogenous construct. Although a transgene construct can be made up of any nucleic acid sequences, for use in the disclosed transgenic fish it is preferred that the transgene constructs combine expression sequences operably linked to a sequence encoding an expression product. The transgenic construct also preferably includes other components that aid expression, stability or integration of the construct into the genome of a fish. As used herein, components of a transgene construct referred to as being operably linked or operatively linked refer to components being so connected as to allow them to function together for their intended purpose. For example, a promoter and a coding region are operably linked if the promoter can function to result in transcription of the coding region.

Expression sequences are used in the disclosed transgene constructs to mediate expression of an expression product encoded by the construct. As used herein, expression sequences include promoters, upstream elements, enhancers, and response elements. It is preferred that the expression sequences used in the disclosed constructs be homologous expression sequences. As used herein, in reference to components of transgene constructs used in the disclosed transgenic fish, homologous indicates that the component is native to or derived from the species or type of fish involved. Conversely, heterologous indicates that the component is neither native to nor derived from the species or type of fish involved.

As used herein, expression sequences are divided into two main classes, promoters and enhancers. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

Enhancers regulate the expression of genes. This effect has been observed and utilized in so-called enhancer trap approach where introduction of a construct containing a reporter gene operably linked to a promoter is expressed only when the construct inserts into the domain of an enhancer (O'Kane et al., 1987; Allen et al., 1988; Kothary et al., 1988; Gossler et al., 1989; Parinov et al., 2004). In such cases, the expression of the construct is regulated according to the pattern of the newly associated enhancer. Transgenic constructs having only a minimal or a short promoter can be used in the disclosed transgenic fish to drive expression of oncogene into various tissues. The advantage of the enhancer trap methodology is that the same construct can be used in order to induce tumors in different tissues. Thus, screening a transgenic population, transformed using such a construct, and yield animals or animal lines with histologically different types of tumors.

For expression of encoded peptides or proteins, a transgene construct also needs sequences that, when transcribed into RNA, mediate translation of the encoded expression products. Such sequences are generally found in the 5' untranslated region of transcribed RNA. This region corresponds to the region on the construct between the transcription initiation site and the translation initiation site (that is, the initiation codon). The 5' untranslated region of a construct can be derived from the 5' untranslated region normally associated with the promoter used in the construct, the 5' untranslated region normally associated with the sequence encoding the expression product, the 5' untranslated region of a gene unrelated to the promoter or sequence encoding the expression product, or a hybrid of these 5' untranslated regions. Preferably, the 5' untranslated region is homologous to the fish into which the construct is to be introduced. Preferred 5' untranslated regions are those normally associated with the promoter used.

Transgene constructs for use in the disclosed transgenic fish encode a reporter protein (for detection and quantitation of expression). As used herein, a reporter protein is any protein that can be specifically detected when expressed. Reporter proteins are useful for detecting or quantitating expression from expression sequences. For example, operatively linking nucleotide sequence encoding a reporter protein to a tissue specific expression sequences allows one to carefully study lineage development. In such studies, the reporter protein serves as a marker for monitoring developmental processes, such as cell migration. Many reporter proteins are known and have been used for similar purposes in other organisms. These include enzymes, such as β-galactosidase, luciferase, and alkaline phosphatase, that can produce specific detectable products, and proteins that can be directly detected. Virtually any protein can be directly detected by using, for example, specific antibodies to the protein.

The use of reporter proteins that are directly detectable without requiring the addition of exogenous factors are preferred for detecting or assessing gene expression during zebrafish embryonic development. A transgenic zebrafish embryo, carrying a construct encoding a reporter protein and a tissue-specific expression sequences, can provide a rapid real time in vivo system for analyzing spatial and temporal expression patterns of developmentally regulated genes.

The disclosed transgene constructs preferably include other sequences which improve expression from, or stability of, the construct. For example, including a polyadenylation signal on the constructs encoding a protein ensures that transcripts from the transgene is processed and transported as mRNA. The identification and use of polyadenylation signals in expression constructs is well established. It is preferred that homologous polyadenylation signals be used in the transgene constructs.

In accordance with the above principles, the oncogene is operably linked to a promoter. Preferably the promoter is an organ- or tissue- (including cell-) specific promoter. Most preferably, the promoter is the keratin-8 (krt8) promoter which is specific for epithelial cells (Gong et al., 2002). Preferably, the promoter is a shortened krt8 promoter (Parinov et al., 2004) or a minimal promoter than can be used as an enhancer trap. Other examples of promoters include promoters of the recombination activating genes (RAG), including RAG1 and RAG2; LCK, which encodes a T-cell-specific, non-receptor tyrosine kinase; IgM enhancer elements, and CD2. Several promoters that direct tissue-restricted expression have been identified, for example, zebrafish RAG1 (Jessen et al., 1999) and zebrafish RAG2 (Jessen et al., 2001) for lymphoid tissues, and Islet-1 for neural-specific expression (Motoike et al., 2000), PDX-1 and Insulin for pancreas (Huang et al., 2001). Promoters having at least about 70% identity, at least about 80% identity, and further at least about 90% identity to the nucleotide sequences of the tissue-specific promoters described herein are also envisioned, provided that they promote transcription of the oncogene to which they are operably linked. Since most mammalian promoters are found not to work well in fish, then the genomic regulatory sequences of the zebrafish, fugu or other fish species often must be specifically cloned upstream, within, and downstream of the coding sequence of interest, which may be accomplished by procedures routine to those skilled in the art.

As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary join two protein coding regions, contiguous and in reading frame. Since enhancers may function when separated from the promoter by several kilobases and intron sequences may be of variable lengths, some nucleotide sequences may be operably linked but not contiguous.

The construct further preferably comprises a marker or a reporter gene. In a preferred embodiment, the oncogene is preceded by a reporter gene, such as a fluorescent protein gene (e.g., EGFP, GFP, RFP, BFP, YFP, or dsRED2) or a luciferase protein gene. In a most preferred embodiment, the marker is enhanced green fluorescent protein (EGFP) (Zhang et al., 1996). EGFP is preferred because of the high sensitivity of the reporter protein. In the preferred embodiment, a fusion of the marker and the oncogene is prepared such that the fused gene is under control of the promoter. It is preferred that the marker comprises the N-terminus of the fusion protein and the oncogene product comprises the C-terminus of the fusion protein. In this preferred embodiment, the construct comprises a chimeric transgene gene comprising promoter-marker-oncogene.

Although, the use of specific markers has been disclosed and discussed herein, the present invention is in no way limited to the specifically disclosed markers. Many additional reporter proteins are known and have been used for similar purposes. These include enzymes, such as β-galactosidase, luciferase, chloramphenicol acytransferase, β-glucuronidase and alkaline phosphatase, that can produce specific detectable products, and proteins that can be directly detected. Virtually any protein can be directly detected by using, for example, specific antibodies to the protein. Any reporter which can be readily detected may be used in place of the EGFP. Additional markers (and associated antibiotics) that are suitable for either positive or negative selection of eukaryotic cells are disclosed, inter alia, in Sambrook and Russell (2001), *Molecular Cloning*, 3$^{rd}$ Ed., Cold Spring Harbor Laboratory Press, Cold Spring Harbor, N.Y., and Ausubel et al. (1992), *Current Protocols in Molecular Biology*, John Wiley & Sons, including periodic updates. Any of the disclosed markers, as well as others known in the art, may be used to practice the present invention.

A construct may be made by using the promoter sequences upstream of the coding region of the gene. The genomic promoter sequences are first cloned upstream of the marker, for example EGFP, to see if they can drive expression of this fluorescent marker in a tissue-specific fashion during development, and if so, then the same sequences are used to drive the expression of K-ras and other oncogenes. Similar procedures may be utilized for construction of other, e.g., zebrafish, organ- and tissue-specific promoters, which are well known to those of skill in the art, such as those cloned from the genes encoding tyrosine hydroxylase for the dopaminergic nervous system, MYO-D for the muscle system, and MPO or PU.1 for the myeloid system.

In a preferred embodiment, the construct of the present invention comprises the zebrafish krt8 promoter, EGFP as the marker and an oncogene, such as zK-ras. The zebrafish krt8 promoter is advantageously used because it drives expression of the transgene, i.e., oncogene, in skin epithelial tissues, and to various other tissues due to an enhancer trap effect (Parinov et al., 2004). If a different promoter is utilized it is preferred that such promoter also exhibits an enhancer trap effect. If an enhancer trap is not normally associated with a particular promoter, an enhancer trap system may also be part of the construct. In this aspect, the construct further comprises an enhancer trap system comprising a minimal promoter element operably linked to a given DNA binding protein (e.g. Gal4-VP 16 fusion) and a reporter gene product under regulation of corresponding activating sequences (e.g. UAS, upstream activating sequences specific for Gal4) such that the transgenic construct can be randomly inserted and/or transposed in the genome of fish using an "enhancer trap" strategy that facilitates random expression patterns that are dependent on properties of regulatory regions (e.g. enhancers and/or repressors) that act at the site of integration. For instance, enhancer trap lines can be created in zebrafish using transposable elements (including, but not limited to, Sleeping Beauty, the Tc1/mariner-like family, (Grabher et al., 2003; Ivies et al., 1999; Parinov et al., 2004) and maize Ac/Ds (see U.S. provisional patent application Ser. No. 60/681,447 filed on 17 May 2005, incorporated herein by reference) and fish that demonstrate expression patterns of interest can be propagated and utilized identically to other transgenic fish.

The transgene may be included in a vector for delivery. A vector, as used herein and as known in the art, refers to a nucleic acid construct that includes genetic material designed to direct transformation (i.e., the process whereby genetic material of an individual cell is altered by incorporation of exogenous DNA into its genome) of a targeted cell. A vector may contain multiple genetic elements positionally and sequentially oriented, i.e., operably linked with other necessary or desired elements such that the nucleic acid in a cassette can be transcribed and, if desired, translated in the microinjected, single-cell fertilized embryo.

Recombinant expression vectors may be constructed by incorporating the above-recited nucleotide sequences within a vector according to methods well known to the skilled artisan and as described, for example, in references cited herein. A wide variety of vectors are known that have use in the invention. Suitable vectors include plasmid vectors, viral vectors, including retrovirus vectors (e.g., see Miller et al., 1993), adenovirus vectors (e.g., see Erzurum et al., 1993; Zabner et al., 1994; Davidson et al., 1993) adeno-associated virus vectors (e.g., see Flotte et al., 1993), herpesvirus vectors (e.g., see Anderson et al., 1993), and lentivirus vectors (e.g., see Lever, 2000). Vectors can carry transposons (Davidson et al., 2003; Fadool et al., 1998; Kawakami et al., 2000; Parinov et al., 2004; U.S. provisional patent application Ser. No. 60/681,447) or Sce-I meganuclease sites (Thermes et al., 2002) to increase the efficiency of transgenesis.

A further aspect of the present invention is the use of constructs or vectors to produce transgenic fish. As used herein, transgenic fish refers to fish, or progeny of a fish, into which an exogenous construct has been introduced. A fish into which a construct has been introduced includes fish which have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded. However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor or founder fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

The disclosed constructs and methods can be used with any type of fish. As used herein, fish refers to any member of the classes collectively referred to as pisces. It is preferred that fish belonging to species and varieties of fish of commercial or scientific interest be used. Such fish include, but are not limited to, salmon, trout, tuna, halibut, catfish, zebrafish, medaka, carp, tilapia, goldfish, and loach.

The most preferred fish for use with the disclosed constructs and methods is zebrafish, *Danio rerio*. Zebrafish are an increasingly popular experimental animal since they have many of the advantages of popular invertebrate experimental organisms, and include the additional advantage that they are vertebrates. Another significant advantage of zebrafish is that, like Caenorhabditis, they are largely transparent (Kimmel, 1989). General zebrafish care and maintenance is described by Streisinger (1984) and Westerfield (2000).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, 1989). Other fish with some or all of the same desirable characteristics are also preferred.

Transgenic fish are prepared using the constructs described herein. In one embodiment, a method includes introducing the nucleic acid, i.e., construct or vector described herein, into a fertilized fish egg (i.e., including a fish embryo) or an unfertilized fish egg nucleic acid. When a fertilized fish egg is used, the method includes developing the fish embryo into a transgenic fish. When the nucleic acid is introduced into a non-fertilized egg, the method includes fertilizing the egg and developing the fish embryo into a transgenic fish. The nucleic acid may be introduced into the egg by a variety of methods known to the art, including mechanical methods, chemical methods, lipophilic methods, retroviral infection methods, and electroporation. Exemplary mechanical methods include, for example, microinjection. Exemplary chemical methods include, for example, use of calcium phosphate or DEAE-Dextran. Exemplary lipophilic methods include use of liposomes and other cationic agents for lipid-mediated transfection. Such methods are generally well known to the art and many of such methods are described in, for example, *Gene Transfer Methods: Introducing DNA into Living Cells and Organisms*, (P. A. Norton and L. F. Steel, eds., Biotechniques Press, 2000); and *Current Protocols in Molecular Biology* (Ausubel et al., eds., John Wiley & Sons). Microinjection techniques involving fish are further more fully described in, for example, Chen and Powers (1990) and Fletcher and Davis (1991). Electroporation techniques involving fish are further more fully described in, for example, Powers et al. (1992) and Lu et al. (1992). Techniques for introducing DNA into fish eggs or embryos by infection with retroviral vectors, such as pantropic retroviral vectors, are further described in, for example, Burns et al. (1993).

The vector or other nucleic acid comprising the transgene may be introduced into an unfertilized egg or a fertilized egg at a desired stage of development. Multiple vectors, each encoding different transgenes as described herein may be used. When using a fertilized egg, or embryo, it is preferred to introduce the nucleic acid into the embryo (i.e., at the one-cell stage of development). However, the nucleic acid may also be administered at later stages of development, including the two-cell stage, four-cell stage, etc. Therefore, the nucleic acid may be introduced into the morula, blastula, etc. At least one isolated nucleic acid molecule incorporating the above-described transgenic construct is introduced into the zygote. Additionally, when the nucleic acid is introduced into an egg at later stages of development, at least one isolated nucleic acid molecule incorporating the above-described transgenic construct is introduced into at least one cell of the, for example, morula, blastula, etc.

Fish eggs may be obtained from the appropriate fish by standard methods. Many of the fish may be purchased commercially from, for example, pet stores. Fertilized eggs may be obtained by methods known to the art. For example, a desired number of appropriately aged fish, such as about three to about twelve month old fish, with a desired ratio of females to males (such as about 2:1) may be placed in an appropriately sized container, such as a tank. Eggs may be collected by, for example, placing the fish in a nuptial chamber in the tank for an appropriate time after mating, such as about 10 to 60 minutes. Such methods are described in, for example, Culp et al. (1991). Alternatively, fish eggs may be artificially fertilized by methods known to the skilled artisan. One skilled in the art is familiar with other methods of obtaining such fertilized fish eggs.

After introducing the nucleic acid construct into the fish egg or embryo, the fish egg or embryo is provided with an environment conducive to development into an adult fish. Such an environment may include, for example, growth at 28.5° C. in E3 egg water for 15 days followed by introduction into circulating system water by day 16 (Westerfield, 2000).

Fish harboring a transgene can be identified by any suitable means. The use of reporter proteins that, like EGFP, are directly detectable without requiring the addition of exogenous factors are preferred for detecting or assessing gene expression during zebrafish embryonic development. A transgenic zebrafish embryo, carrying a construct encoding a reporter protein can provide a rapid real time in vivo system for analyzing spatial and temporal expression patterns of developmentally regulated genes. Alternatively, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques. Preferred techniques for identifying transgenic zebrafish are described in the examples.

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level, different tissues of a fish can be dissected and expression can be assayed in the separate tissue samples. Such an assessment can be performed when using almost any expression product. This technique is commonly used in transgenic animals and is useful for assessing tissue-specific expression. Expression can be determined biochemically, enzymatically, phenotypically or in a model fish.

This technique can also be used to assess expression during the course of development by assaying for the expression product at different developmental stages. Where detection of the expression product requires fixing of the sample or other treatments that destroy or kill the developing embryo or fish, multiple embryos must be used. This is only practical where the expression pattern in different embryos is expected to be the same or similar. This is the case when using the disclosed transgenic fish having stable and predictable expression. A more preferred way of assessing the pattern of expression of a transgene during development is to use an expression product that can be detected in living embryos and animals.

In zebrafish, the nervous system and other organ rudiments appear within 24 hours of fertilization. Since the nearly transparent zebrafish embryo develops outside its mother, the origin and migration of lineage progenitor cells can be monitored by following expression of an expression product in transgenic fish. In addition, the regulation of a specific gene can be studied in these fish.

Further aspects of the present invention are the production of immortal tumor cell lines from the tumors induced in the transgenic fish and the immortal tumor cell lines so produced. In one embodiment, an immortal tumor cell line is produced by expressing the oncogene in fish to produce a tumor, isolating cells from the tumor and culturing the isolated tumor cells to produce an immortal tumor cell line. The production of immortal tumor cell lines from the tumor cells isolated from the fish tumors is performed using conventional techniques well known to persons skilled in the art. Suitable techniques are described in *Culture of Animal Cells: A Manual of Basic Techniques*, 5$^{th}$ Ed. (R. I. Freshney, Wiley-Liss, Inc., New York, 2005), *Animal Cell Culture: A Practical Approach*, 3$^{rd}$ Ed. (J. Masters (ed.), Oxford University Press, Oxford, 2000) and *Animal Cell Culture* (J. W. Pollard and J. M. Walker, Humana Press, Totowa, N.J., USA, 1990). In one embodiment, tumor cells are isolated from the tumors developed in fish that were injected with Pkrt8-EGFP-K-rasB (V12) construct at 1 cell-stage. The isolated cells are capable of long-term maintenance in the culture and are immortal. For example, one cell line successfully passed through over 20 sequential passages maintaining rapid proliferation rate of 1 cell division every ~24-36 hours. This tumor cell line maintained EGFP expression in the culture throughout the multiple passages and after transplantation into the sublethally irradiated host. Transplanted fish developed tumors in various organs confirming the malignant nature of the tumor cell line. Thus, cells from Pkrt8-EGFP-K-rasB(V12) induced tumors are capable of long-term proliferation in culture conditions. Transplantation of the cultured cells into sublethally γ-irradiated host leads to tumor formation and spread.

The tumor cells lines produced in accordance with the present invention are useful as a model for tumor progression and metastasis. The tumor cells lines can be additionally transformed with different constructs or otherwise modified and transplanted into a host and used to study transplantation and various interactions between the transplanted cells and the host. In addition, the host with the transplanted immortal tumor cell line is useful to screen compounds for inhibiting tumor progression or metastasis. Also, the immortal tumor cell lines are useful to screen compounds for inhibiting tumor cell growth. The screening of compounds using the transplanted host or immortal tumor cell lines can be carried out using techniques well known to persons skilled in the art, including techniques similar to those described herein for screening compounds using transgenic fish.

Transgenic fish of the present invention (or host with transplanted immortal tumor cell line or immortal tumor cell line) are useful to screen compounds for modulating effects on proteins encoded by genes of interest. In this embodiment, a method of screening for drugs or agents that modulate oncogene-mediated, or otherwise induced, neoplastic or hyperplastic transformation, or that modulate the sensitivity of transgenic cells to treatments with radiation or chemotherapy, is provided. A method comprises (a) contacting or otherwise exposing a transgenic fish (e.g., an adult transgenic fish or a transgenic fish embryo) described herein with a test drug or agent, wherein the genome of the transgenic fish has stably integrated therein nucleic acid comprising an oncogene operably linked to a promoter; (b) determining if the test drug or agent suppresses or enhances oncogene-mediated neoplastic or hyperplastic transformation, or modulates the sensitivity of transgenic cells to treatments with radiation or chemotherapy; and (c) classifying the test drug or agent as a drug or agent that modulates oncogene-mediated neoplastic or hyperplastic transformation, or that modulates the sensitivity of transgenic cells to treatments with radiation or chemotherapy, if the test drug or agent suppresses or enhances oncogene-mediated neoplastic or hyperplastic transformation or modulates the sensitivity of transgenic cells to treatments with radiation or chemotherapy. As mentioned herein, the modulation may include suppressing, or otherwise decreasing, or enhancing, or otherwise stimulating, oncogene-mediated neoplastic or hyperplastic transformation, including the rate of oncogene-mediated neoplastic or hyperplastic transformation, or sensitivity of transgenic cells to treatments with radiation or chemotherapy. The test compounds can be administered to transgenic fish harboring the construct. Alternatively and preferably, the compound can be dosed in the water holding the transgenic fish, with the fish taking up substances via their contact surfaces, e.g., gills, skin and gut.

A variety of test compounds can be evaluated in accordance with the present invention. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin and Ellman, 1992; DeWitt et al., 1993), peptoids (Zuckermann, 1994), oligocarbamates (Cho et al., 1993), and hydantoins (DeWitt et al., 1993). An approach for the synthesis of molecular libraries of small organic molecules with a diversity of 104-105 as been described (Carell et al., 1994a; Carell et al., 1994b).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, 1997). Other exemplary methods for the synthesis of molecular libraries can be found in the art, for example in Erb et al. (1994), Horwell et al. (1996) and Gallop et al. (1994).

Libraries of compounds may be presented in solution (e.g., Houghten et al., 1992), or on beads (Lam et al., 1991), chips (Fodor et al., 1993), bacteria (U.S. Pat. No. 5,223,409), spores (U.S. Pat. No. 5,223,409), plasmids (Cull et al., 1992) or on phage (Scott and Smith, 1990; Devlin et al., 1990; Cwirla et al., 1990; Felici et al., 1991). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

The test drug or agent is typically identified from a large-scale, robotically-driven screen of thousands of compounds to identify a drug or agent thought to have the ability to modulate oncogene-mediated neoplastic or hyperplastic transformation, or modulate the sensitivity of transgenic cells to treatments with radiation or chemotherapy. Such screens are routine, and these, and other screening methods, are well known by those of skill in the art. The test drug or agent may suppress, or otherwise alter, or enhance expression of oncogene RNA and/or the oncogenic protein product, or RNA or protein expression of other genes involved in the oncogenic transformation process. Additionally, the test drug or agent may inhibit or stimulate the activity of other molecules involved, directly or indirectly, in the neoplastic/hyperplastic transformation process, or in the sensitivity of transgenic cells to treatments with radiation or chemotherapy. A wide variety of drugs or agents, such as described herein and others, may be tested in the screening methods of the present invention.

The test drugs or agents are typically administered in an amount and for a time necessary to suppress, or otherwise alter, or enhance oncogene-mediated neoplastic or hyperplastic transformation. Such amounts and times may be determined by the skilled artisan by known standard procedures. Transgenic fish are typically contacted with the test drug or agent at a desired time.

In one embodiment of the invention, determining if the test drug or agent suppresses, or otherwise alters, or enhances oncogene-mediated neoplastic or hyperplastic transformation may be performed by measuring the amount and/or size of tumors formed in the fish and/or measuring the rate of onset of tumor formation. Other indicators of oncogene-mediated, or otherwise induced, neoplastic or hyperplastic transformation, or modulation of the sensitivity of transgenic cells to treatments with radiation or chemotherapy, may also be measured. For example, when reporter gene-oncogene fusion constructs are used, reporter gene expression may be determined using methods well known by those of skill in the art and as described herein. For instance, utilizing a tissue-specific promoter operably linked to a EGFP-oncogene fusion construct will permit EGFP fluorescence emitted from the protein specifically expressed in a particular tissue to be determined. Additional visual or other screens for metastatic tumors may also be used.

In yet another form of the invention, methods of identifying mutations that modulate (i.e., enhance, suppress, or otherwise alter) oncogene-mediated, or otherwise induced, neoplastic or hyperplastic transformation, such as the rate of onset of neoplastic or hyperplastic growth, including malignant tumors, are provided. In one form, a method involves use of genetic modifier screens. Such screens take advantage of the forward genetic capabilities of the transgenic fish described herein. Mutations that enhance the rate of onset of malignant tumors may be found, for example, in tumor suppressor genes, oncogenes or other genes involved in the neoplastic or hyperplastic process. Other mutations that alter genomic stability may also enhance the rate of onset of malignant tumors. Mutations that suppress the rate of onset of neoplastic or hyperplastic growth include, for example, proteins required for the malignant phenotype, including proteins that have not yet been identified. Methods for identifying such mutations are described in U.S. published patent application No. 2004/0117867 A1, incorporated herein by reference.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. Such techniques include those disclosed in U.S. Pat. No. 6,080,576.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

With regard to intervention, any compounds which reverse any aspect of a given phenotype or expression of any gene in vivo and which modulates protein activity or binding with binding partner in vitro should be considered as candidates for further development or potential use in humans. Dosages of test agents may be determined by deriving dose-response curves using methods well known in the art.

Figure 5A:
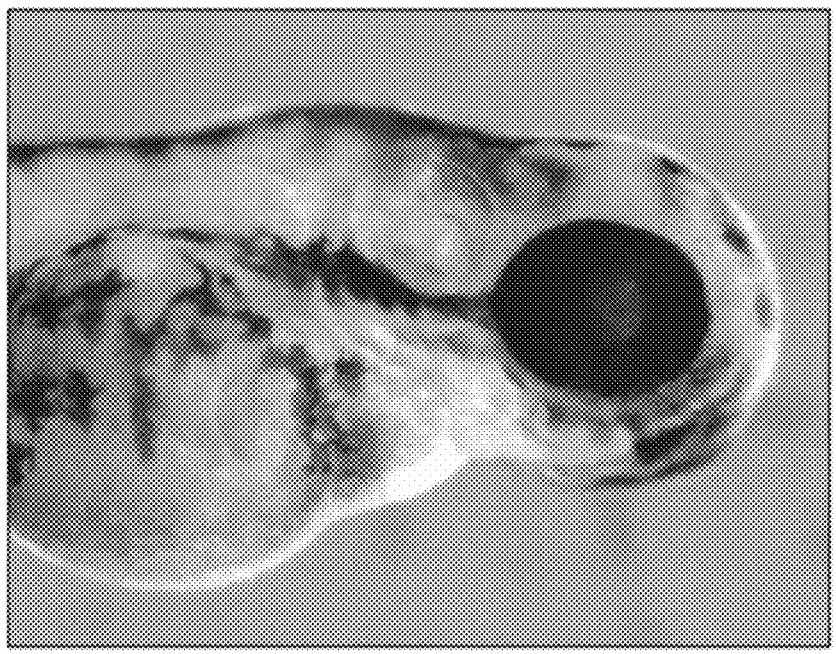
FIG. 5 shows $F_1$ generation of fish carrying stable P-krt8-EGFP-zK-rasB transgene. P-krt8-EGFP control showing normal morphology of the P-krt8-EGFP-positive cells (FIG. 5A). zK-ras(V12)-induced phenotype (FIG. 5B).
Figure 5B:
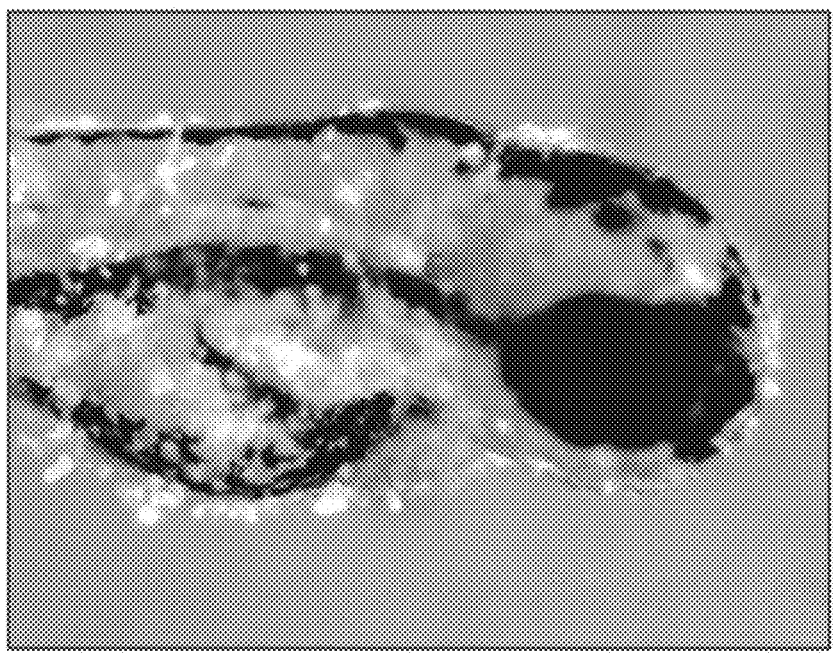

The present invention has several advantages. First, unlike existing cancer models, the present invention enables the screening for phenotypical changes that occur in transgenic cells at a very early stage of development instead of focusing on the dynamics of tumor formation and suppression in the adult fish. The advantages of such an approach are: (1) ~100% of transgenic cells undergo early synchronized neoplastic transformation implying simple detection, reproducible and unambiguous results and (2) the use of embryos instead of adult fish—convenient transparency of the embryo, short experimental ime, significantly less space and drug amount requirements that favor large scale screening. In one embodiment, the successful choice of skin-specific promoter to drive oncogene expression does not result in early lethality which allows the production of a large population of stable transgenic carriers (see, FIG. 5).

Although fish embryos are generally used, adult fish with developed cancer conditions can also be used for various applications. Tumors in adult fish more closely reflect human tumors. The aggressive nature and asynchronous formation of tumors in adult fish can be addressed using inducible expression systems (e.g., Cre/Lox described by Langenau et al., 2005) and fish species that have transparent bodies as adults, e.g., glass fish.

In addition to the use of fish that carry a stably integrated transgene, fish injected with the oncogenic construct can also be used. Microinjection is a simple technique and can be applied on a medium to large scale. This approach has one advantage: individual labeled cells, e.g., individual GFP-labeled cells, that have a characteristic shape can be seen. Injection of the oncogenic construct also induces various cancers in more than 10% of adult fish within the first three months of development (see, FIGS. 3 and 4). Some of these tumors could be hard to maintain as a stable transgene without inducible expression systems due to early lethality of carriers.

The use of the enhancer trap methodology eliminates the necessity of producing numerous constructs with various tissue- or organ-specific promoters (although such constructs can be made if desired) in order to drive the expression of the same transgene in different tissues. An effective enhancer trap approach in zebrafish has been described by Parinov et al. (2004). The enhancer trap patterns are usually narrower compared to the tagged genes, contributing only to a specific subset of cells. Most importantly, enhancer trap lines with virtually unlimited pattern variations can be easily produced using the same DNA constructs. The present invention employs the enhancer trap approach (effect) for combinatorial targeting of tumorogenesis into various tissues in fish. For example, despite using the skin-specific promoter described herein, approximately 15% of this injected with the same krt8-GFP-ras construct develop histologically different tumors in various internal organs by three months of age. The high variation among the obtained tumors can complicate the analysis. Nevertheless, transgenic fish carrying stable transgenes with different expression patterns can be produced. Early lethality of such stable transgenic fish can be prevented using inducible systems.

The expression of oncogenic ras in transgenic fish will cause early developmental lethality in many cases making it problematic to create stable transgenic tumor producing lines and maintaining them through generations. These complications can be overcome using inducible systems (e.g., Cre/Lox described by Langenau et al., 2005, as well as other inducible systems well known to skilled artisans). In such cases, the transgenic lines expressing a reporter (GFP for example) but not the oncogene can be selected in a screen, grown to maturity and the progeny can be obtained. The oncogene expression can be induced when desired by supplying the Cre-recombinase either pan-embryonically through injection or infection or by crossing with a transgenic fish carrying and expressing Cre gene in its genome.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al.,

*Molecular Cloning,* 2nd Ed. (Cold Spring Harbor Laboratory Press, Cold Spring Harbor, N.Y., 1989); Sambrook and Russell, *Molecular Cloning,* 3rd Ed. (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes,* (Academic Press, New York, 1992); Guthrie and Fink, *Guide to Yeast Genetics and Molecular Biology* (Academic Press, New York, 1991); Harlow and Lane, *Antibodies,* (Cold Spring Harbor Laboratory Press, Cold Spring Harbor, N.Y., 1998); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); Riott, *Essential Immunology,* 6th Edition, (Blackwell Scientific Publications, Oxford, 1988); Hogan et al., *Manipulating the Mouse Embryo,* (Cold Spring Harbor Laboratory Press, Cold Spring Harbor, N.Y., 1986); Westerfield, M., *The zebrafish book. A guide for the laboratory use of zebrafish* (*Danio rerio*), 4th Ed., (Univ. of Oregon Press, Eugene, Oreg., 2000).

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Constructs and Microinjections

Zebrafish K-rasB was amplified using RT PCR with primers: Kras1: ggagccaaGCGG CCGCatgaccgaatataagcttgtg (SEQ ID NO:9) and Kras2: ggaaggaaGCGGCCGCtcacattaatgcacatt ttgttttg (SEQ ID NO:10) digested with NotI restriction endonuclease and cloned into NotI site of ETconstruct (Parinov et al 2004), carrying EGFP gene under 480 bp krt8 promoter (P-krt8-EGFP-TAA(stop)-K-rasB). Oligonucleotides: ctgtacaagtTaagcggcGgcatgac-cgaatataagcttgtggtc gtgggagctgTaggcg (SEQ ID NO:11) and KRR: cgcctAcagctcccacgaccacaagcttatattcggtcatgcCg ccgcttAacttgtacag (SEQ ID NO:12) were used for site-directed mutagenesis in order to remove TAA stop codon and change the 12aa of K-ras to V (oncogenic form). As a result the mRNA product transcribed from partial krt8 promoter is the fusion protein of EGFP and K-RasB-V12 (P-krt8-EGFP-K-rasB-V12).

5-10 pg of plasmid DNA were injected into zebrafish embryos at the 1-2-cell stage. The actual concentration of DNA was empirically adjusted to produce 50% embryo survival rate.

Drug Tests

Drugs from BIOMOL® ICCB Known Bioactives Library Cat #2840 were used for drug tests. Drugs were diluted in standard fish water from the 5-mg/ml DMSO stock solutions. The injected embryos were sorted at 8 hours post fertilization (hpf) and the normally developing were selected for drug treatment. Ten to fifteen embryos per well were plated into 24-well microtiter plate and overlayed with 1.5 ml drug solution at 10 hpf. Embryos were incubated in the dark at 28° C. The results were observed every day until 5 days post fertilization (dpf).

Image Analysis

A SMZ1500 Stereoscopic Zoom Microscope (Nikon) equipped with the epi-fluorescence attachment and DXM1200F digital camera (Nikon) with original software was used for image analysis.

Example 2

Zebrafish K-rasB Coding Sequence

Zebrafish K-ras was amplified using designed PCR primers based on the zgc:85725 cDNA sequence (GenBank accession BC078646; GI:50925043) (Strausberg et al., 2002) as described in Example 1. The cloned sequence contained 7 single-nucleotide substitutions compared to the published GenBank sequence, none of which lead to amino acid changes. The amplified product encoding 188 amino acids is 96% identical (181/188 aa) and 99.5% homologous to human K-ras2 protein isoform b (FIG. 1).

Example 3

Fusion Construct of K-rasB EGFP

A fusion construct between N-terminal enhanced green fluorescent protein (EGFP) and C-terminal oncogenic (V12) zK-rasB was made. The expression was controlled using 480 bp zebrafish krt8 promoter (Gong et al., 2002; Parinov et al., 2004). This promoter normally drives expression early in cells of the EVL and later in skin epithelia. Besides, this promoter was successfully used for enhancer trapping (Parinov et al., 2004). This latter property is used to target tumorigenesis into various tissues. The nucleic acid sequence is set forth in Table 1 and the protein sequence is set forth in Table 2. The sequences of EGFG are underlined and the sequences of zK-rasB are bolded. The modified codon 12 of Ras and the corresponding amino acid (V12) are underlined. The egfp stop codon has been mutated (double underlined) in the active construct and it remained intact in the control. The construct was microinjected into 1-cell stage zebrafish embryo.

TABLE 1

Nucleotide Sequence of the Promoter krt8-EGFP-zK-RasB(V12) Oncogene (SEQ ID NO: 13)
acaatgcaactgttcagctcaggggggaaaaatgccctgccagatccaaacggctggcaaaagtgaatggaaaaaagc ctttcattaatgtgaaagttgctgcgcgccccacccagataaaaagagcagaggttaacatgctctctacggctgtc TABLE 1-continued Nucleotide Sequence of the Promoter krt8-EGFP-zK-RasB(V12) Oncogene cagccaaccagatactgaggcagaaacacaccgctggcagatggtgagagctacactgtcttttccagagtttcta ctggaatgcctgtcctcaagtctcaagcctctcctttgcattctctcattccacctggggcaaagccccaggctgggt gtgacaacatttatcttaccactttctctctgtacctgtctaacaggtagggtgtgtgtgagagtgcgtatgtgtgc aagtgcgtgtgtgtgagagcagtcagctccaccctctcaagagtgtgtataaaattggtcagccagctgctgaga gacacgcagagggactttgactctcctttgtgagcaacctcctccactcactcctctctcagagagcactctcgtac ctccttctcagcaactcaaagacacaggatccaccggtcgccacc<u>atggtgagcaagggcgaggagctgttcaccgg</u>

<u>ggtggtgcccatcctggtcgagctggacggcgacgtaaacggccacaagttcagcgtgtccggcgagggcgagggcg</u>

<u>atgccacctacggcaagctgaccctgaagttcatctgcaccaccggcaagctgcccgtgcctggcccaccctcgtg</u>

<u>accaccctgacctacggcgtgcagtgcttcagccgctaccccgaccacatgaagcagcacgacttcttcaagtccgc</u>

<u>catgcccgaaggctacgtccaggagcgcaccatcttcttcaaggacgacggcaactacaagacccgcgccgaggtga</u>

<u>agttcgagggcgacacc</u>ctggtgaaccgcatcgagctgaagggcatcgacttcaaggaggacggcaacatcctgggg cacaagctggagtacaactacaacagccacaacgtctatatcatggccgacaagcagaagaacggcatcaaggtgaa cttcaagatccgccacaacatcgaggacggcagcgtgcagctcgccgaccactaccagcagaacacccccatcggcg acggccccgtgctgctgcccgacaaccactacctgagcacccagtccgccctgagcaaagaccccaacgagaagcgc gatcacatggtcctgctggagttcgtgaccgccgccgggatcactctcggcatggacgagctgtacaa<u>gtTa</u>agcgg cggc<u>atgaccgaatataagcttgtggtcgtgggagctg</u>Taggcgtaggcaaaagcgctctcaccatccaactcatcc agaaccactttgtggatgaatatgacccGactatagaggactcgtacaggaagcaggtggtgattgacggagaGacg tgtctactggacatcctggacactgcaggtcaggaggaGtacagtgccatgagggaccagtacatgaggacaggaga gggcttcctctgtgtctttgccatcaataacacCaagtccttCgaggacattcaccactacagggagcagataaagc gagtaaaggactcTgaggacgtccccatggttctggtggggaataagtgtgatcttcagtcccacaatgtggactcc aaAcaggctcaggatttagcacgcagctacggcatcccatttatagagacctcagcaaagacaagacagggtgtgga cgacgcgttttatactttagtccgagaaatccggaaacacaaggagaagatgagcaaggagggcaaaaagaaaaaga agaaatccaaaacaaaatgtgcattaatgtga

TABLE 2

The Amino Acid Sequence of the EGFP-K-RAS Fusion Protein (SEQ ID NO: 14)
<u>MVSKGEELFTGVVPILVELDGDVNGHKFSVSGEGEGDATYGKLTLKFICTTGKLPVPWPTLVTTLTYGVQCFSRYPD</u>

<u>HMKQHDFFKSAMPEGYVQERTIFFKDDGNYKTRAEVKFEGDTLVNRIELKGIDFKEDGNILGHKLEYNYNSHNVYIM</u>

<u>ADKQKNGIKVNFKIRHNIEDGSVQLADHYQQNTPIGDGPVLLPDNHYLSTQSALSKDPNEKRDHMVLLEFVTAAGIT</u>

<u>LGMDELYKLSGG</u>MTEYKLVVVGA<u>V</u>GVGKSALTIQLIQNHFVDEYDPTIEDSYRKQVVIDGETCLLDILDTAGQEEYS

AMRDQYMRTGEGFLCVFAINNTKSFEDIHHYREQIKRVKDSEDVPMVLVGNKCDLQSHNVDSKQAQDLARSYGIPFI

ETSAKTRQGVDDAFYTLVREIRKHKEKMSKEGKKKKKKSKTKCALM

Example 4

Figure 2B:
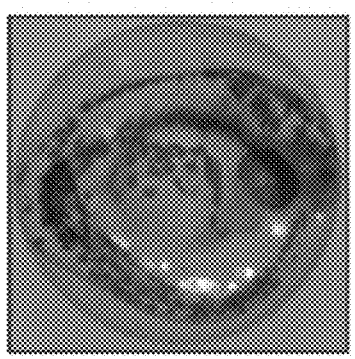
FIGS. 2b and 2c show neoplastic phenotype induced by EGFP-K-rasB(V12) expression.
Figure 2C:
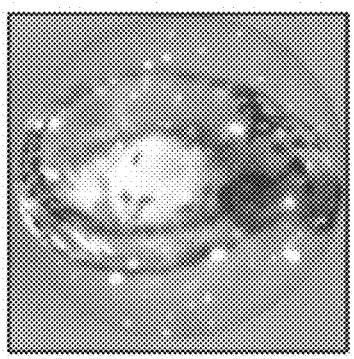

Cells Expressing the P-krt8-EGFP-K-rasB(V12) Transgene Undergo Early Neoplastic Transformation Analyses of the effects produced by the transgene were mainly focused on changes in shape and behavior of the GFP-positive skin epithelial cells (specific expression from krt8 promoter). Embryos injected with a control construct P-krt8-EGFP-TAA(stop)-K-rasB(V12), containing a stop codon between EGF and K-ras coding sequences, produced normal looking skin epithelial cells (FIG. 2a) (Gong et al., 2002; Parinov et al., 2004). Contrary to the control, EGFP-positive cells in embryos, injected with the P-krt8-EGFP-K-rasB(V12) construct, developed abnormal appearance by 24 hpf. At 48 hpf abnormalities became more apparent: most skin epithelial cells acquired distinctive rounded shape (FIG. 2b, many grew large, some began losing contacts with the embryo and separated. At 72 hpf most of the cells detached and remained around the embryo retained in the chorionic sac (FIG. 2c). Virtually all transgenic skin cells shed by 5 dpf, only some internal body cells remained GFP-positive. (Ectopic transgene expression in these cells was likely triggered by the enhancer trap effect.) Muscle cells, that were normally narrow and fiber-like in control, acquired star-like architecture and grew larger. Neurons formed abnormal processes besides growing larger. Notochord cells grew slightly larger looked anatomically similar to the control. The transformation rate correlated with level of the transgene expression. On one hand, stronger GFP expression associated with early transformation. On the other hand, a small number of normally looking skin epithelial cells that expressed hardly detectable levels of EGFP could still found at 3-5 dpf.

High mortality among the injected fish was observed during the first 2 weeks. Approximately 15% of the fish, which survived after injection, developed tumors in various internal organs by 1-3 months of age (FIG. 3). These tumors strongly correlate with the transgene expression.

Example 5

Tumorogenesis in $F_0$ Fish

Figure 4A:
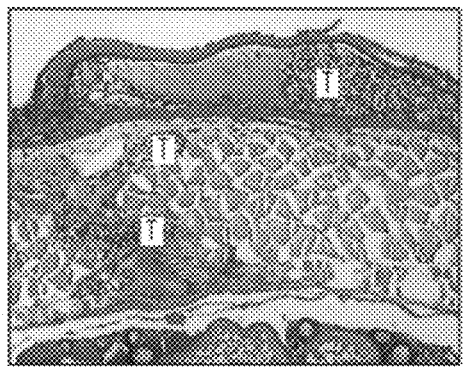
FIGS. 4A and 4B show fish1 (FIGS. 3G, 3H): metastatic cancer spread of unknown origin into various tissues.
Figure 4B:
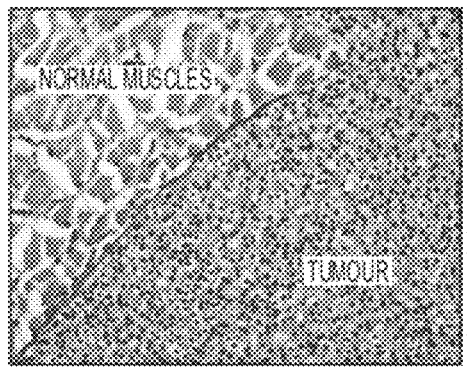
Figure 4C:
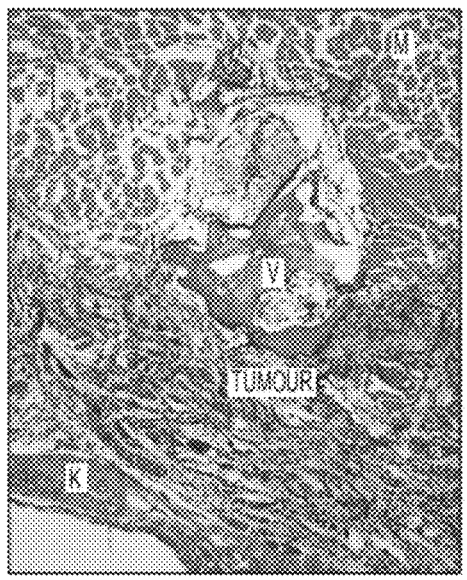
FIG. 4C shows fish2 (FIGS. 3F, 3E): metastatic fibrosarcoma spread into various tissues.
Figure 4D:
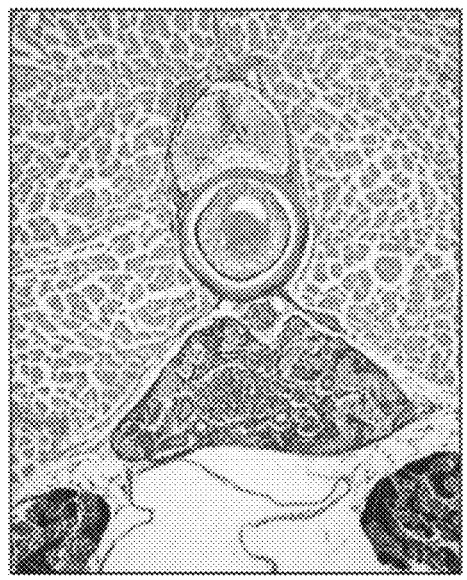
FIG. 4D shows healthy fish, control. V—vertebra; M—muscle; K—kidney; T—tumor.

Fifteen percent of the fish injected with the Ras-EGFP construct develop tumors in various tissues at 1-3 months age (FIG. 3). Affected fish can be easily identified by hemorrhages. These tumors are highly malignant showing vast multiple metastases into various tissues and organs (FIGS. 4A, 4B, 4C). Cancers arising in $F_0$ fish are of various histological origin. Due to metastasis it is hard to identify the original tumor site. However, since each fish carries only one type of cancerous cells (by anatomy), it is unlikely that these tumors have independent origins but rather resulted from metastatic spread from the original site. The GFP expression is always associated with the tumors. On the other hand, strong GFP expression can be observed in the tissues that have no apparent tumors. Nevertheless, all tissues expressing high level of Ras-EGFP transgene always have abnormal anatomy. For example, expression in the brain (FIG. 3C, 3D) leads to abnormal development but no apparent tumor formation is observed.

To summarize the above, expression of the P-krt8-EGFP-zK-RasB(V12) in fish can be used to induce tumors of various histological origin. Ras-induced cancers in fish are characterized by aggressive growth rate and metastasis. Therefore, expression of P-krt8-EGFP-zK-RasB(V12) using various tissue specific promoters or enhancer-trap strategy in promising for modeling cancers in fish. Early onset and aggressive nature of these tumors implies the necessity to apply inducible expression systems (e.g. Cre/lox (Langenau et al., 2005)).

Example 6

Stable Transgenic $F_1$ Line Carrying the P-krt8-EGFP-zk-RasB(V12) Construct in its Genome Exhibits Neoplastic Transformation of Skin Cells and Can Produce Next Generation Fish injected with P-krt8-EGFP-zK-RasB(V12) construct ($F_0$ founders) were raised and their progeny ($F_1$) was analyzed for GFP fluorescence. We isolated few $F_1$ families that carry stable krt8-EGFP-zK-RasB(V12) transgene. GFP-positive skin cells in these stable transgenic fish (FIG. 5) are similar to the cells in fish that were injected with the construct (FIG. 2b, c): cells lose their flat morphology typical to the krt8-GFP cells, they form clusters instead of making an even layer, divide uncontrollably and loose contacts with the body surface. Unlike in the fish injected with the construct that shed all GFP-positive skin cells by 4-5 dpf, in the stable transgenic fish new cells are being produced to replace the shed cells (they can be found on the body even after 5 days). Transgenic fish, expressing EGFP-zK-RasB(V12) only in the skin cells, can grow until maturity and produce transgenic progeny. Therefore, it is possible to generate enough embryos for large-scale screening.

Example 7

Model Evaluation Using Known Tumor Suppressive Drugs

To evaluate feasibility of the model for drug discovery, a mini-screening was performed using selected compounds from BIOMOL® ICCB Known Bioactives Library. The embryos injected with EGFP-zK-rasB(V12) construct were treated with various drugs in 24-well microtiter plates. The drugs were administered into the standard fish water starting at 10 hpf. Concentration of drugs was proposed based on data from a preliminary screening for developmental toxicity. Effects of the drugs on these cells in this preliminary screen are shown in Table 3.

TABLE 3

Model Evaluation Using Known Tumor Suppressive Drugs

| Drug | Concentration | Effects |
| --- | --- | --- |
| PD98059 | 3 µg/ml | preserves the epithelial characteristics of surface cells |
| U0126 | 3 µg/ml | NO* |
| PP2 | 3 µg/ml | Keeps cells flat and attached but doesn't stop growth |
| PP1 | 3 µg/ml | Keeps cells flat and attached but doesn't stop growth |
| LY294002 | 3 µg/ml | NO |
| Wortmannin | 1 µg/ml | ? |
| Manumycin A | 3 µg/ml | NO |
| L-744,832 | 10 µg/ml | NO |
| GW-5074 | 1 µg/ml | Cytotoxic, non-specific effects |
| ZM336372 | 10 µg/ml | NO |
| Lovastatin | 0.003 µg/ml | Cytotoxic, non-specific effects |
| Cocktails | | |
| PD98059/PP2 | 1.5 µg/ml/1.5 µg/ml | +++ Toxicity |
| AG879/PP1 | 0.01 µg/ml/1.5 µg/ml | ++ Toxicity |

*NO means no specific effect observed

Figure 2D:
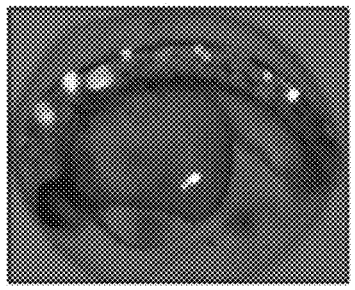
FIGS. 2d-2g show drug effects for PP2 (FIGS. 2d and 2e) and PD98059 (FIGS. 2f and 2g).
Figure 2E:

Two Src family kinase inhibitors, PP1 and PP2, produced similar effects (FIGS. 2d and 2e). The transformed cells maintained flat shape while continued to grow. This produced enlarged star-shaped cells that remained attached to the embryo. The effect was observed at 3 µg/ml concentration which is toxic for developing embryo. At 1 µg/ml concentration toxicity was tolerable, however, the specific effect on the EGFP-positive cells was also considerably reduced. It has been earlier demonstrated (Nam et al., 2002) that PP2 reduced metastatic spread of cancer by restoring E-cadherin-mediated cell adhesion system. This may be one of the mechanism the effects observed in the zebrafish model.

Figure 2F:
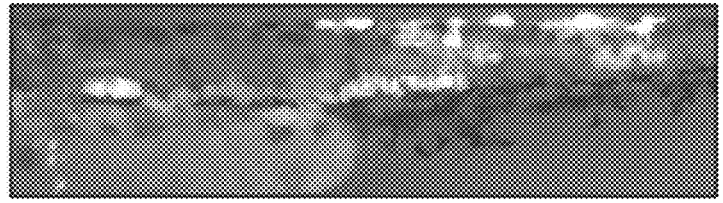
Figure 2G:
Figure 3A:
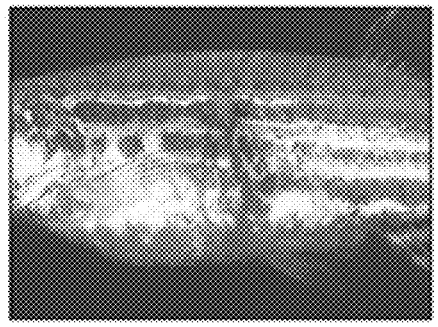
FIGS. 3A(3B), 3C(3D), 3F(3E) and 3G(3H) show examples of tumors in four different $F_0$ fish with the corresponding GFP images.
Figure 3B:
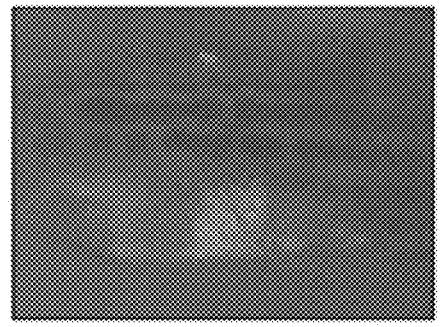
FIG. 3 shows tumor formation in $F_0$ adult fish that were injected with P-krt8-EGFP-zK-rasB transgene.
FIGS. 3C(3D) show fish that demonstrates severe brain abnormalities associated with the transgene expression. All fish develop extensive hemorrhages at the places of tumor growth.
FIG. 3E shows that tumor growth is closely associated with transgene expression. The fish in FIGS. 3A(3B), 3C(3D), and 3G(3H) are 2 months old. The fish in FIGS. 3F(3E) is a 3 month old fertile female. The fish in FIGS. 3G(3H) developed visible condition (extensive hemorrhage) at 1 month of age.
Figure 3C:
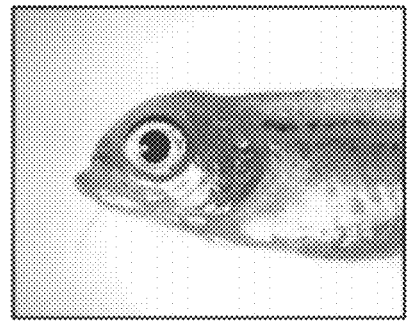
Figure 3D:
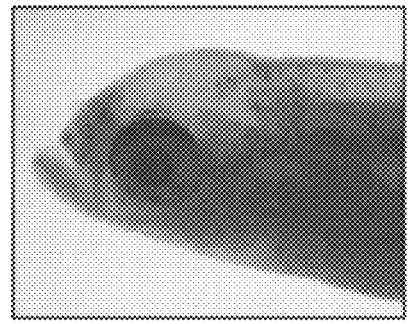
Figure 3E:
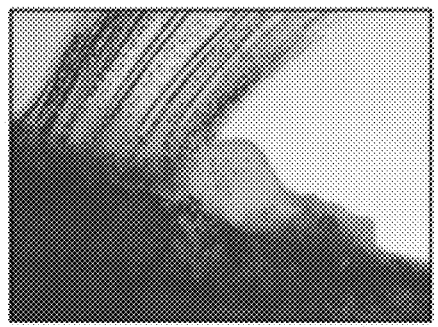
Figure 3F:
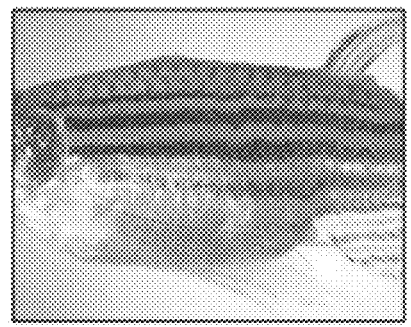
Figure 3G:
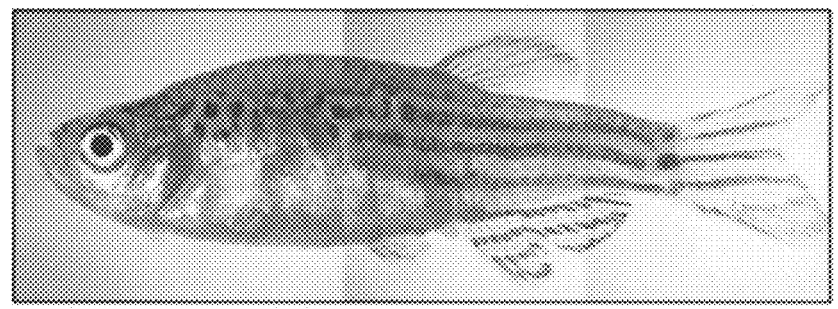
Figure 3H:

Inhibitor of mitogen-activated protein kinase kinase (MEK) PD98059 (Alessi et al., 1995; Dudley et al., 1995; Guyton et al., 1996) at 3 ng/ml concentration strongly impairs growth of the EGFP-positive cells. By 72 hpf cells are smaller, maintain flat shape and remain attached to the embryo (FIGS. 2f and 2g). The toxic effects of this drug on development become serious only at 10 ng/ml.

Example 8

Establishing a Zebrafish Tumor Cell Line

Figure 6A:
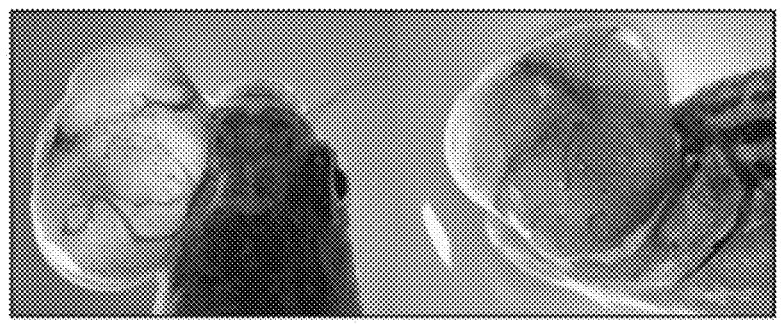
FIG. 6A shows the fish used to produce this tumor cell line prior tumor isolation. An embryo was injected with Pkrt8-EGFP-K-rasB(V12) construct at 1-cell stage and by the age of 2 months it developed the large tumor of the eye. The tumor was GFP-positive. This tumor was isolated and the cells were grown in culture.
Figure 6B:
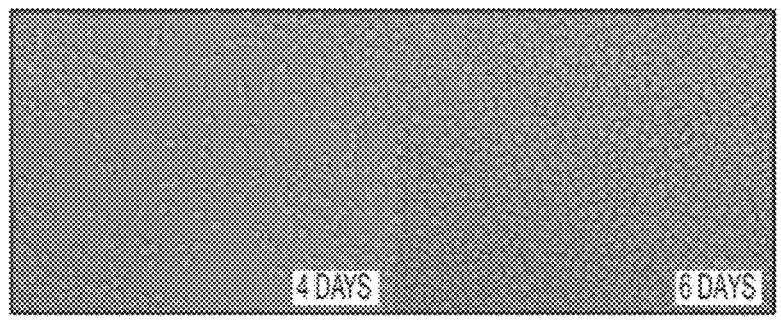
FIG. 6B shows an example of the cultured cells at the $4^{th}$ and $6^{th}$ day after the new passage illustrating rapid proliferation.
Figure 6C:
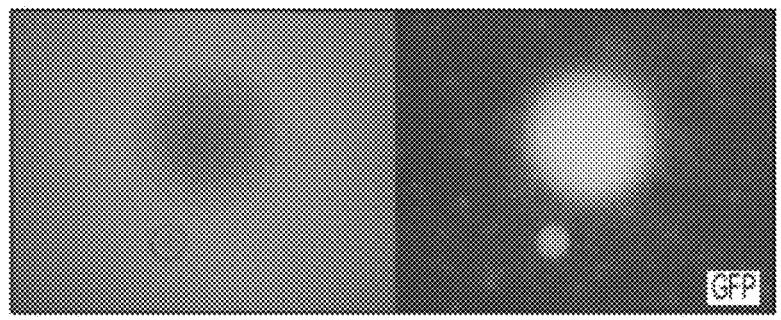
FIG. 6C shows loss of contact inhibition in the cell line. Cells were grown to confluence until foci were evident (8 day after the passage). The foci formation shown in this example exhibits bright EGFP fluorescence. The cultured cells emit weak GFP fluorescence that is harder to observe in the monolayer surrounding the much brighter foci.
Figure 6D:
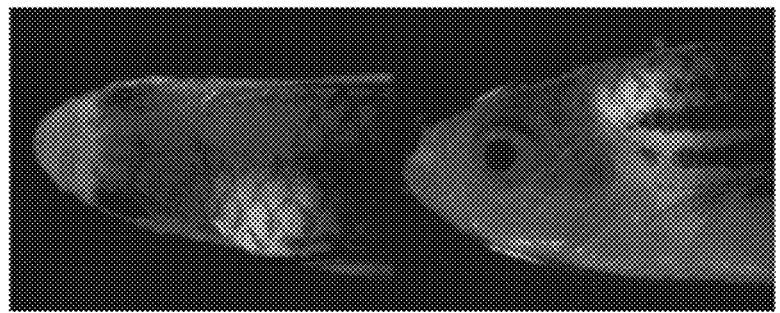
FIG. 6D shows tumors in fish injected with the cultured cells (12 days post injection). GFP-positive tumor formations are evident in the muscles.
Figure 6E:
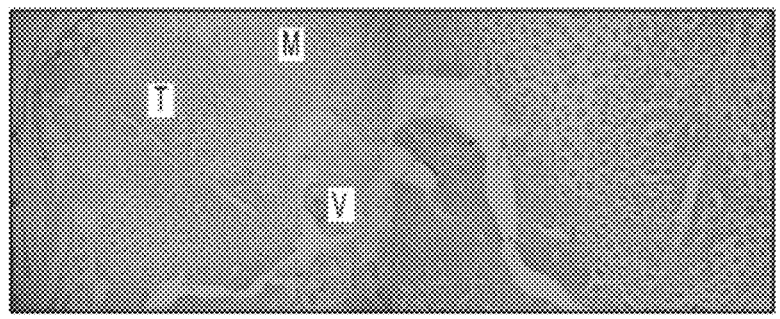
FIG. 6E shows histological analysis of tumor formation in the fish shown in FIG. 6D. Paraffin embedded sections stained with hematoxylin/eosin. v—vertebra; m—muscles; t—tumor.

One of the fish that was injected with Pkrt8-EGFP-K-rasB (V12) construct at 1 cell-stage developed a large eye tumor by the age of 2 months (FIG. 6A). The tumor was isolated and dissected with scissors, sterilized with ethanol, washed several times in sterile 1× Hank's balanced salt solution and 1% antibiotic-antimycotic mix and triturated with razor blades. Sample was then incubated for 30 min at 28° C. in 1 ml 1× Hank's balanced salt solution with 0.14 units/ml Liberase Blendzyme 3. After complete dissociation, cells were washed in 1× Hank's balanced salt solution and 8 ml growth media LFD (50% L-15/15% F-12/35% DMEM) with 10% FBS and 1% antibiotic-antimycotic mix were added, and the mixture was incubated at 28° C. in culture flask. After 2 days, cells were washed with growth media to remove dead and not attached cells, and new media was replaced. Cells were grown until monolayer confluence, detached with LFD without FBS, resuspended in growth media and $10^6$ cells seeded in 10 ml flask.

This cell line was passed through a series of passages as follows: After reaching 2-4×$10^7$ population the cells were detached and resuspended (1:20) in fresh media and ~$10^6$ cells were passed in 10 ml flask every 5-6 days (2-4×$10^7$ cells). The cells successfully passed through 24 such passages maintaining rapid proliferation rate of 1 cell division in less than 36 hours. The cell line was frozen in LFD/10%FBS/10% DMSO in liquid nitrogen after $5^{th}$, $8^{th}$, $10^{th}$ and $24^{th}$ passages.

Example 9

Transplantation of Tumor Cell Line into Irradiated Fish

Adult wild type fish were irradiated with 24 gamma rays 2 days before transplantation. 7×$10^7$ cells ($21^{st}$ passage) were detached with LFD without FBS, washed twice with 1× Hank's balanced salt solution and resuspended in 1× Hank's balanced salt solution until $10^5$ cell/µl. Two days after irradiation, 10 µl of the concentrated cell suspension ($10^6$ cells) were injected intraperitoneally or intramuscularly into sublethally irradiated wild-type recipients using 25 µl Hamilton syringe. Other sublethally irradiated wild-type recipients were injected with 10 µl 1× Hank's balanced salt solution (control population). The GFP-positive tumor formations were found not only at the injection site but also in the locations separated far from the injection site suggestive of an active spreading of the tumor cells. Moreover, the tumor cells and tumor foci were found in different tissues and organs within the same host.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods, fish, immortal tumor cell lines and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Ahuja, H. G. et al. (1990). "The pattern of mutational involvement of RAS genes in human hematologic malignancies determined by DNA amplification and direct sequencing." *Blood* 75:1684-1690.

Alessi, D. R. et al. (1995). "PD098059 is a specific inhibitor of the activation of mitogen-activated protein kinase in vitro and in vivo." *J Biol Chem* 270:27489-27494.

Allen et al. (1988). "Transgene as probes for active chromosomal domains in mouse development." *Nature* 333:852-855.

Altschul, S. F. et al., (1990). "Basic local alignment search tool." *J Mol Biol* 215:403-410.

Altschul, S. F. et al. (1997). "Gapped BLAST and PSI-BLAST: a new generation of protein database search programs." *Nucleic Acids Res* 25:3389-3402.

Andersen, J. K. et al. (1993). "Herpesvirus-mediated gene delivery into the rat brain: specificity and efficiency of the neuron-specific enolase promoter." *Cell Mol Neurobiol* 13:503-515.

Baliga, S. N. (2001). "Promoter analysis by saturation mutagenesis." *Biol. Proced. Online* 3:64-69.

Bos, J. L. (1989). "Ras oncogenes in human cancer: a review." *Cancer Res* 49:4682-4689.

Bunin, B. A. and Ellman, J. A. et al. (1992). "A general and expedient method for the solid-phase synthesis of 1,4-benzodiazepine derivatives." *J. Am. Chem. Soc.* 114:10997-10998.

Burns, J. C. et al. (1993). "Vesicular stomatitis virus G glycoprotein pseudotyped retroviral vectors: concentration to very high titer and efficient gene transfer into mammalian and nonmammalian cells." *Proc Natl Acad Sci USA* 90:8033-8037.

Carell, E. et al. (1994a). "A Novel Procedure for the Synthesis of Libraries Containing Small Organic Molecules." *Angew. Chem Int. Ed. Engl.* 33:2059-2061.

Carell, E. et al. (1994b). "A Solution-Phase Screening Procedure for the Isolation of Active Compounds from a Library of Molecules." *Angew. Chem. Int. Ed. Engl.* 33:2061-2064.

Chen, T. T. and Powers, D. A. (1990). "Transgenic fish." *Trends Biotechnol* 8:209-215.

Cho, C. Y. et al. (1993). "An Unnatural biopolymer." *Science.* 261:1303-1305.

Cull, M. G. et al. (1992). "Screening for Receptor Ligands Using Large Libraries of Peptides Linked to the C Terminus of the lac Repressor." *Proc Natl Acad Sci USA* 89:1865-1869.

Culp, P. et al. (1991). "High-frequency germ-line transmission of plasmid DNA sequences injected into fertilized zebrafish eggs." *Proc Natl Acad. Sci USA* 88:7953-7957.

Cwirla, S. E. et al. (1990). "Peptides on Phage: A Vast Library of Peptides for Identifying Ligands." *Proc. Natl. Acad. Sci. USA* 87:6378-6382.

Davidson, A. E. et al. (2003). "Efficient gene delivery and gene expression in zebrafish using the Sleeping Beauty transposon." *Dev Biol* 263:191-202.

Davidson, B. L. et al. (1993). "A model system for in vivo gene transfer into the central nervous system using an adenoviral vector." *Nature Genetics* 3:219-223.

Devlin, J. L. et al. (1990). "Random Peptide Libraries: A Source of Specific Protein Binding Molecules." *Science* 249:404-406.

DeWitt, S. H. et al. (1993). "Diversomers": An Approach to Nonpeptide, Nonoligomeric Chemical Diversity." *Proc. Natl. Acad. Sci. USA* 90:6909-6913.

Dudley, D. T. et al. (1995). "A synthetic inhibitor of the mitogen-activated protein kinase cascade." *Proc Natl Acad Sci USA* 92:7686-7689.

Erb, E. et al. (1994). "Recursive Deconvolution of Combinatorial Chemical Libraries." *Proc. Natl. Acad. Sci. USA* 91:11422-11426.

Erzurum, S. C. et al. (1993). "Protection of human endothelial cells from oxidant injury by adenovirus-mediated transfer of the human catalase cDNA." *Nucleic Acids Res* 21:1607-1612.

Fadool, J. M. et al. (1998). "Transposition of the mariner element from *Drosophila mauritiana* in zebrafish." *Proc Natl Acad Sci USA* 95:5182-5186.

Felici, F. et al. (1991). "Selection of antibody ligands from a large library of oligopeptides expressed on a multivalent exposition vector." *J Mol. Biol.* 222:301-310.

Fletcher, G. L., and Davis, P. L. (1991). "Transgenic fish for aquaculture." In *Genetic Engineering*, Setlow, J. K., ed., Plenum Press.

Flotte, T. R. et al. (1993). "Stable in vivo expression of the cystic fibrosis transmembrane conductance regulator with an adeno-associated virus vector." *Proc Natl Acad Sci USA* 90:10613-10617.

Fodor, S. et al. (1993). "Multiplexed biochemical assays with biological chips." *Nature* 364:555-556.

Gallop, M. A. et al. (1994). "Applications of combinatorial technologies to drug discovery. 1. Background and peptide combinatorial libraries." *J. Med. Chem.* 37:1233-1251.

Gong, Z. et al. (2001). "Green fluorescent protein (GFP) transgenic fish and their applications." *Genetica* 111:213-225.

Gong, Z. et al. (2002). "Green fluorescent protein expression in germ-line transmitted transgenic zebrafish under a stratified epithelial promoter from keratin8." *Dev Dyn* 223:204-215.

Gossler et al. (1989). "Mouse Embryonic Stem Cells and Reporter Constructs to Detect Developmentally Regulated Genes." *Science* 244:463-465.

Grabher, C. et al. (2003). "Transposon-mediated enhancer trapping in medaka." *Gene* 322:57-66.

Guyton, K. Z. et al. (1996). "Mitogen-activated protein kinase (MAPK) activation by butylated hydroxytoluene hydroperoxide: implications for cellular survival and tumor promotion." *Cancer Res* 36:3480-3465.

Horwell, D. et al (1996). 'Targeted' molecular diversity: design and development of non-peptide antagonists for cholecystokinin and tachykinin receptors." *Immunopharmacology* 33:68-72.

Houghten, R. A. et al. (1992). "The use of synthetic peptide combinatorial libraries for the identification of bioactive peptides." *Biotechniques* 13:412-421.

Huang, H. et al. (2001). "Pdx-1 knockdown reduces insulin promoter activity in zebrafish." *Genesis* 30:134-136.

Ivies, Z. et al. (1999). "Genetic applications of transposons and other repetitive elements in zebrafish." *Methods in Cell Biology* 60:99-131.

Jessen, J. R. et al. (1999). "Artificial chromosome transgenesis reveals long-distance negative regulation of rag1 in zebrafish." *Nat Genet* 23:15-16.

Jessen, J. R. et al. (2001). "Concurrent expression of recombination activating genes 1 and 2 in zebrafish olfactory sensory neurons." *Genesis* 29:156-162.

Johnson, L. et al. (2001). "Somatic activation of the K-ras oncogene causes early onset lung cancer in mice." *Nature,* 410:1111-1115.

Kaeakami, K. et al. (2000). "Identification of a functional transposase of the Tol2 element, an Ac-like element from the Japanese medaka fish, and its transposition in the zebrafish germ lineage." *Proc Natl Acad Sci USA* 97:11403-11408.

Kennedy, B. N. et al. (2001). "Isolation of a zebrafish rod opsin promoter to generate a transgenic zebrafish line expressing enhanced green fluorescent protein in rod photoreceptors." *J Biol Chem* 276:14037-14043.

Kimmel, C. B. (1989). "Genetics and Early Development of Zebrafish." *Trends Genet* 5:283-288.

Kothary et al. (1988). "A transgene containing lacZ inserted into the dystonia locus is expressed in neural tube." *Nature* 335:435-437.

Lam, K. S. (1997). "Application of combinatorial library methods in cancer research and drug discovery." *Anticancer Drug Des.* 12:145-167.

Lam, K. S. et al. (1991). "A new type of synthetic peptide library for identifying ligand-binding activity." *Nature* 354:82-84.

Langenau, D. M. et al. (2005). "Cre/lox-regulated transgenic zebrafish model with conditional myc-induced T cell acute lymphoblastic leukemia." *Proc Natl Acad Sci USA* 102: 7369-7374.

Lever, A. M. (2000). "Lentiviral vectors: progress and potential." *Curr Opin Mol Ther* 2:488-496.

Long, Q. et al. (1997). "GATA-1 expression pattern can be recapitulated in living transgenic zebrafish using GFP reporter gene." *Development* 124:4105-11.

Lu, J. K. et al. (1992). "Integration, expression and germ-line transmission of foreign growth hormone genes in medaka (*Oryzias latipes*)." *Molec Mar Biol Biotechnol* 1:366-375.

Miller, A. D. et al., (1993). "Use of retroviral vectors for gene transfer and expression." *Methods of Enzymology* 217:581-599.

Moss, J. B. et al. (1996). "Green Fluorescent Protein Marks Skeletal Muscle in Murine Cell Lines and Zebrafish." *Gene* 173:89-98.

Motoike, T. et al. (2000). "Universal GFP reporter for the study of vascular development." *Genesis* 28:75-81.

Nam, J. S. et al. (2002). "Src family kinase inhibitor PP2 restores the E-cadherin/catenin cell adhesion system in human cancer cells and reduces cancer metastasis." *Clin Cancer Res.* 8:2430-2436.

O'Kane, et al. (1987). "Detection in situ of Genomic Regulatory Elements in *Drosophila.*" *Proc. Natl. Acad. Sci. USA* 84:9123-9127.

Parinov, S. et al. (2004). "Enhancer trap transposable element as a tool for identification of developmentally regulated genes in zebrafish in vivo." *Dev Dyn.* 231:449-459.

Park, H. C. et al. (2000). "Analysis of upstream elements in the HuC promoter leads to the establishment of transgenic zebrafish with fluorescent neurons." *Dev Biol* 227:279-293.

Powers, D. A. et al. (1992). "Electroporation: a method for transferring genes into the gametes of zebrafish (*Brachydanio rerio*), channel catfish (*Ictalurus punctatus*), and common carp (*Cyprinus carpio*)." *Molec Mar Biol Biotechnol* 1:301-308.

Scott, J. K. and J. P. Smith (1990). "Searching for Peptide Ligands with an Epitope Library." *Science* 249:386-390.

Strausberg et al. 2002. Generation and initial analysis of more than 15,000 full-length human and mouse cDNA sequences. *Proc. Natl. Acad. Sci. U.S.A.* 99:16899-16903.

Streisinger (1984). Attainment of Minimal Biological Variability and Measurements of Genotoxicity: Production of Homozygous Diploid Zebra Fish. *Natl. Cancer Inst. Monogr.* 65:53-58.

Thermes, V. et al. (2002). "I-SecI meganuclease mediates highly efficient transgenesis in fish." *Mech Dev* 118:91-98.

Westerfield, M. (2000). *The Zebrafish Book: A guide for the laboratory use of Zebrafish (Danio rerio)*, 4th ed., University of Oregon Press, Eugene.

Zabner, J. et al. (1994). "Safety and efficacy of repetitive adenovirus-mediated transfer of CFTR cDNA to airway epithelia of primates and cotton rats." *Nature Genetics* 6:75-83.

Zhang, G. et al. (1996). "An enhanced green fluorescent protein allows sensitive detection of gene transfer in mammalian cells." *Biochem Biophys Res Commun* 227:707-711.

Zuckermann, R. N. (1994). "Discovery of nanomolar ligands for 7-transmembrane G-protein-coupled receptors from a diverse N-(substituted)glycine peptoid library." *J. Med. Chem.* 37:2678-2685.

What is claimed is:

1. A method of preparing an immortal tumor cell line comprising isolating cells from a tumor of a transgenic fish and culturing the isolated tumor cells under conditions suitable to produce an immortal tumor cell line, wherein the transgenic fish is selected from the group consisting of a transgenic fish in which its genome has stably integrated therein a nucleic acid that comprises an oncogene operably linked to a promoter and a transgenic fish in which some cells have incorporated therein said nucleic acid, wherein the nucleic acid has inserted into a domain of an enhancer and acts as an enhancer trap, wherein the oncogene is an oncogenic K-ras gene, wherein the oncogene is expressed in tissues corresponding to a trapped enhancer in the transgenic fish and wherein the oncogene induces a tumor in the transgenic fish.

2. The method of claim 1, wherein the promoter is organ-specific promoter or a tissue-specific promoter.

3. The method of claim 2, wherein the tissue-specific promoter is a keratin-8 (krt8) promoter.

4. The method of claim 1, wherein the oncogene is a fish oncogene.

5. The method of claim 1, wherein the oncogene is a mammalian oncogene.

6. The method of claim 1, wherein the oncogene is selected from the group consisting of (i) an oncogenic zK-rasB, and (ii) an oncogenic homologue of an oncogenic zK-rasB.

7. The method of claim 1, wherein the oncogene is fused to a reporter gene.

8. The method of claim 7, wherein the reporter gene is selected from the group consisting of a fluorescent protein gene, luciferase, β-galactosidase, chloramphenicol, acytransferase, β-glucuronidase, and alkaline phosphatase.

9. The method of claim 8, wherein the fluorescent protein gene is EGFP.

10. The method of claim 1, the nucleic acid comprises a K-ras oncogene operably linked to a krt8 promoter, wherein the K-ras oncogene is fused to an enhanced green fluorescent protein gene.

11. The method of claim 10, the K-ras oncogene is zK-rasB (V12) and the krt8 promoter is a zebrafish krt8 promoter.

12. A method of preparing an immortal tumor cell line comprising isolating cells from a tumor of a transgenic fish and culturing the isolated tumor cells under conditions suitable to produce an immortal tumor cell line, wherein the transgenic fish is selected from the group consisting of a transgenic fish in which its genome has stably integrated therein a nucleic acid that comprises an oncogene operably linked to a promoter and a transgenic fish in which some cells have incorporated therein said nucleic acid, wherein the promoter is a minimal promoter, wherein the nucleic acid acts as an enhancer trap, wherein the oncogene is an oncogenic K-ras gene, wherein the oncogene is expressed in tissues corresponding to a trapped enhancer in the transgenic fish and wherein the oncogene induces a tumor in the transgenic fish.

13. The method of claim 12, wherein the minimal promoter is a minimal organ-specific promoter or a minimal tissue-specific promoter.

14. The method of claim 13, wherein the minimal tissue-specific promoter is a minimal keratin-8 (krt8) promoter.

15. The method of claim 12, the nucleic acid comprises a K-ras oncogene operably linked to a minimal krt8 promoter, wherein the K-ras oncogene is fused to an enhanced green fluorescent protein gene.

16. The method of claim 15, the K-ras oncogene is zK-rasB (V12) and the minimal krt8 promoter is a zebrafish minimal krt8 promoter.

* * * * *

```
SEQUENCE LISTING

<160> NUMBER OF SEQ ID NOS: 14

<210> SEQ ID NO 1
<211> LENGTH: 188
<212> TYPE: PRT
<213> ORGANISM: Homo sapiens

<400> SEQUENCE: 1

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gly Glu Glu Tyr
        50                  55                      60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gln Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 2
<211> LENGTH: 188
<212> TYPE: PRT
<213> ORGANISM: Danio rerio

<400> SEQUENCE: 2

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gly Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Gln Ser His Asn Val Asp Ser Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gln Val Asp Asp Ala Phe Tyr Thr Leu Val
145                 150                 155                 160

Arg Glu Ile Arg Lys His Lys Glu Lys Met Ser Lys Glu Gly Lys Lys
                165                 170                 175

Lys Lys Lys Lys Ser Lys Thr Lys Cys Ala Leu Met
            180                 185
```

<210> SEQ ID NO 3
<211> LENGTH: 188
<212> TYPE: PRT
<213> ORGANISM: Kirsten murine sarcoma virus

<400> SEQUENCE: 3

```
Met Thr Glu Tyr Lys Leu Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
```

```
                    145                 150                 155                 160
Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185

<210> SEQ ID NO 4
<211> LENGTH: 189
<212> TYPE: PRT
<213> ORGANISM: Homo sapiens

<400> SEQUENCE: 4

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 5
<211> LENGTH: 189
<212> TYPE: PRT
<213> ORGANISM: Homo sapiens

<400> SEQUENCE: 5

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110
```

-continued

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 6
<211> LENGTH: 189
<212> TYPE: PRT
<213> ORGANISM: Homo sapiens

<400> SEQUENCE: 6

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 7
<211> LENGTH: 188
<212> TYPE: PRT
<213> ORGANISM: Homo sapiens

<400> SEQUENCE: 7

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

```
Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Val His Leu Tyr
                 85                  90                  95

Arg Glu Gln Ile Lys Arg Val Asp Ser Asp Asp Val Pro Met Val
            100                 105                 110

Leu Val Gly Asn Ile Cys Asp Leu Ala Arg Thr Val Asp Thr Lys Gln
            115                 120                 125

Ala Gln Glu Leu Ala Arg Ser Tyr Gly Ile Glu Phe Val Glu Thr Ser
130                 135                 140

Ala Lys Thr Arg Gln Gly Val Glu Asp Ala Phe Tyr Thr Leu Val Arg
145                 150                 155                 160

Glu Ile Arg His Tyr Arg Met Lys Lys Leu Asn Ser Arg Glu Asp Arg
                165                 170                 175

Lys Gln Gly Cys Leu Gly Val Ser Cys Glu Val Met
            180                 185

<210> SEQ ID NO 8
<211> LENGTH: 188
<212> TYPE: PRT
<213> ORGANISM: Danio rerio

<400> SEQUENCE: 8

Met Thr Glu Tyr Lys Leu Val Val Val Gly Ala Val Gly Val Gly Lys
  1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gly Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Gln Ser His Asn Val Asp Ser Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Gln Val Asp Asp Ala Phe Tyr Thr Leu Val
145                 150                 155                 160

Arg Glu Ile Arg Lys His Lys Glu Lys Met Ser Lys Glu Gly Lys Lys
                165                 170                 175

Lys Lys Lys Lys Ser Lys Thr Lys Cys Ala Leu Met
            180                 185

<210> SEQ ID NO 9
<211> LENGTH: 37
<212> TYPE: DNA
<213> ORGANISM: Artificial
<220> FEATURE:
<223> OTHER INFORMATION: Oligonucleotide primer

<400> SEQUENCE: 9
ggagccaagc ggccgcatga ccgaatataa gcttgtg                            37
```

<210> SEQ ID NO 10
<211> LENGTH: 41
<212> TYPE: DNA
<213> ORGANISM: Artificial
<220> FEATURE:
<223> OTHER INFORMATION: Olignoculceotide primer

<400> SEQUENCE: 10
ggaaggaagc ggccgctcac attaatgcac attttgtttt g                 41

<210> SEQ ID NO 11
<211> LENGTH: 61
<212> TYPE: DNA
<213> ORGANISM: Artificial
<220> FEATURE:
<223> OTHER INFORMATION: Olignoulceotide for site-directed mutagenesis

<400> SEQUENCE: 11
ctgtacaagt taagcggcgg catgaccgaa tataagcttg tggtcgtggg agctgtaggc    60
g                                                                  61

<210> SEQ ID NO 12
<211> LENGTH: 61
<212> TYPE: DNA
<213> ORGANISM: Artificial
<220> FEATURE:
<223> OTHER INFORMATION: Olignoulceotide for site-directed mutagenesis

<400> SEQUENCE: 12
cgcctacagc tcccacgacc acaagcttat attcggtcat gccgccgctt aacttgtaca    60
g                                                                  61

<210> SEQ ID NO 13
<211> LENGTH: 1880
<212> TYPE: DNA
<213> ORGANISM: Artificial
<220> FEATURE:
<223> OTHER INFORMATION: Oncogene fusion construct
<220> FEATURE:
<221> NAME/KEY: promoter
<222> LOCATION: (1)..(584)
<223> OTHER INFORMATION: zebrafish krt8 promoter
<220> FEATURE:
<221> NAME/KEY: misc_feature
<222> LOCATION: (585)..(1304)
<223> OTHER INFORMATION: EGFP gene
<220> FEATURE:
<221> NAME/KEY: misc_feature
<222> LOCATION: (1314)..(1880)
<223> OTHER INFORMATION: zK-ras-V12 gene

<400> SEQUENCE: 13
acaatgcaac tgttcagctc aggggggaaaa atgccctgcc agatccaaac ggctggcaaa    60
agtgaatgga aaaagccttt tcattaatgt gaaagttgct cgcgcgcccca cccagataaa   120 aagagcagag gttaacatgc tctctacggc tgtccagcca accagatact gaggcagaaa   180
cacacccgct ggcagatggt gagagctaca ctgtcttttc cagagtttct actggaatgc   240
ctgtcctcaa gtctcaagcc tctccttgca ttctctcatt ccacctgggg caaagcccca   300
ggctgggtgt gacaacattt atcttaccac tttctctctg tacctgtcta acaggtaggg   360
tgtgtgtgag agtgcgtatg tgtgcaagtg cgtgtgtgtg tgagagcagt cagctccacc   420
ctctcaagag tgtgtataaa attggtcagc cagctgctga gagacacgca gagggacttt   480
gactctcctt tgtgagcaac ctcctccact cactcctctc tcagagagca ctctcgtacc   540

```
tccttctcag caactcaaag acacaggatc caccggtcgc caccatggtg agcaagggcg    600
aggagctgtt caccggggtg gtgcccatcc tggtcgagct ggacggcgac gtaaacggcc    660
acaagttcag cgtgtccggc gagggcgagg gcgatgccac ctacggcaag ctgaccctga    720
agttcatctg caccaccggc aagctgcccg tgccctggcc caccctcgtg accaccctga    780
cctacggcgt gcagtgcttc agccgctacc ccgaccacat gaagcagcac gacttcttca    840
agtccgccat gcccgaaggc tacgtccagg agcgcaccat cttcttcaag gacgacggca    900
actacaagac ccgcgccgag gtgaagttcg agggcgacac cctggtgaac cgcatcgagc    960
tgaagggcat cgacttcaag gaggacggca acatcctggg gcacaagctg gagtacaact   1020
acaacagcca caacgtctat atcatggccg acaagcagaa gaacggcatc aaggtgaact   1080
tcaagatccg ccacaacatc gaggacggca gcgtgcagct cgccgaccac taccagcaga   1140
acacccccat cggcgacggc cccgtgctgc tgcccgacaa ccactacctg agcacccagt   1200
ccgccctgag caaagacccc aacgagaagc gcgatcacat ggtcctgctg gagttcgtga   1260
ccgccgccgg gatcactctc ggcatggacg agctgtacaa gttaagcggc ggcatgaccg   1320
aatataagct tgtggtcgtg ggagctgtag gcgtaggcaa aagcgctctc accatccaac   1380
tcatccagaa ccactttgtg gatgaatatg acccgactat agaggactcg tacaggaagc   1440
aggtggtgat tgacggagag acgtgtctac tggacatcct ggacactgca ggtcaggagg   1500
agtacagtgc catgagggac cagtacatga ggacaggaga gggcttcctc tgtgtctttg   1560
ccatcaataa caccagtcc ttcgaggaca ttcaccacta cagggagcag ataaagcgag   1620
taaaggactc tgaggacgtc cccatggttc tggtggggaa taagtgtgat cttcagtccc   1680
acaatgtgga ctccaaacag gctcaggatt tagcacgcag ctacggcatc ccatttatag   1740
agacctcagc aaagacaaga cagggtgtgg acgacgcgtt ttatacttta gtccgagaaa   1800
tccggaaaca caaggagaag atgagcaagg agggcaaaaa gaaaaagaag aaatccaaaa   1860
caaaatgtgc attaatgtga                                               1880
```

<210> SEQ ID NO 14
<211> LENGTH: 431
<212> TYPE: PRT
<213> ORGANISM: Artificial
<220> FEATURE:
<223> OTHER INFORMATION: Oncogene fusion protein

<400> SEQUENCE: 14

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

-continued

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Ser Gly Gly Met Thr Glu Tyr Lys Leu Val Val Val Gly Ala Val Gly
                245                 250                 255

Val Gly Lys Ser Ala Leu Thr Ile Gln Leu Ile Gln Asn His Phe Val
            260                 265                 270

Asp Glu Tyr Asp Pro Thr Ile Glu Asp Ser Tyr Arg Lys Gln Val Val
            275                 280                 285

Ile Asp Gly Glu Thr Cys Leu Leu Asp Ile Leu Asp Thr Ala Gly Gln
    290                 295                 300

Glu Glu Tyr Ser Ala Met Arg Asp Gln Tyr Met Arg Thr Gly Glu Gly
305                 310                 315                 320

Phe Leu Cys Val Phe Ala Ile Asn Asn Thr Lys Ser Phe Glu Asp Ile
                325                 330                 335

His His Tyr Arg Glu Gln Ile Lys Arg Val Lys Asp Ser Glu Asp Val
            340                 345                 350

Pro Met Val Leu Val Gly Asn Lys Cys Asp Leu Gln Ser His Asn Val
            355                 360                 365

Asp Ser Lys Gln Ala Gln Asp Leu Ala Arg Ser Tyr Gly Ile Pro Phe
    370                 375                 380

Ile Glu Thr Ser Ala Lys Thr Arg Gln Gly Val Asp Asp Ala Phe Tyr
385                 390                 395                 400

Thr Leu Val Arg Glu Ile Arg Lys His Lys Glu Lys Met Ser Lys Glu
                405                 410                 415

Gly Lys Lys Lys Lys Lys Lys Ser Lys Thr Lys Cys Ala Leu Met
            420                 425                 430
```